US005824328A

United States Patent [19]
Levy

[11] Patent Number: 5,824,328
[45] Date of Patent: *Oct. 20, 1998

[54] INSECTICIDAL DELIVERY COMPOSITIONS AND METHODS FOR CONTROLLING A POPULATION OF INSECTS IN AN AQUATIC ENVIRONMENT

[75] Inventor: Richard Levy, Fort Myers, Fla.

[73] Assignee: Stockhausen GmbH, Krefeld, Germany

[ * ] Notice: The term of this patent shall not extend beyond the expiration date of Pat. No. 4,818,534.

[21] Appl. No.: 245,816

[22] Filed: May 18, 1994

Related U.S. Application Data

[63] Continuation of Ser. No. 560,286, Jul. 30, 1990, abandoned, which is a continuation of Ser. No. 211,895, Jun. 27, 1988, abandoned, which is a division of Ser. No. 32,532, Apr. 1, 1987, Pat. No. 4,818,534.

[51] Int. Cl.$^6$ .............................. A01N 25/34; A61K 9/14
[52] U.S. Cl. .......................... 424/409; 424/404; 424/405; 424/408; 424/410; 424/484; 424/489; 514/772.1; 514/772.2; 514/772.4; 514/777
[58] Field of Search .................................... 424/405, 409, 424/484, 485, 486, 487, 404, 408, 410, 84, 489; 514/772.1, 772.2, 772.4; 525/54.31, 54.32; 526/930

[56] References Cited

U.S. PATENT DOCUMENTS

| | | | |
|---|---|---|---|
| 3,085,850 | 4/1963 | Egan et al. . | |
| 3,234,125 | 2/1966 | Block et al. | 210/633 |
| 3,253,984 | 5/1966 | Seymour et al. | 514/772.4 |
| 3,253,985 | 5/1966 | Seymour et al. | 514/772.4 |

(List continued on next page.)

FOREIGN PATENT DOCUMENTS

| | | |
|---|---|---|
| 0 050 375 | 4/1982 | European Pat. Off. . |
| 0 140 548 A1 | 5/1985 | European Pat. Off. . |
| 719330 | 12/1954 | United Kingdom . |
| 829565 | 3/1960 | United Kingdom . |
| 922317 | 3/1963 | United Kingdom . |
| 948185 | 1/1964 | United Kingdom . |
| 1156059 | 6/1969 | United Kingdom . |
| 1188736 | 4/1970 | United Kingdom . |
| 1 313 892 | 4/1973 | United Kingdom . |
| 2108517 | 5/1983 | United Kingdom . |
| 2111388 | 7/1983 | United Kingdom . |
| 2 126 591 A | 3/1984 | United Kingdom . |
| 2141023 | 12/1984 | United Kingdom . |
| 2 146 607 A | 4/1985 | United Kingdom . |
| WO 85/01736 | 4/1985 | WIPO . |

OTHER PUBLICATIONS

Derwent Publication Ltd. Abstract No. 85–120188/20 of Japanese Patent JP–A–60 061 504–A; Apr. 1985.
Supplementary European Search Report 89 90 7983; May 8, 1992 and Annex.
Supplementary European Search Report 89 90 8114; Apr. 11, 1992 and Annex.
Supplementary European Search Report 89 90 7927; May 7, 1992 and Annex.
European Search Report No. 88 30 2860.
*The Insecticide, Herbicide, Fungicide Quick Guide*, B.G. Page et al., Thomson Publications, 1987.
*Insect Conrol Guide*, Florida Agricultural Extension Service, Institute of Food and Agricultural Sciences University of Florida, Gainsville.

*Agricultural Chemicals* Book I, “Insecticides, Acaricides and Ovicides”, W. T. Thomas, 1985–1986 Revision, Thomson Publications.

*Agricultural Chemicals* Book II, “Herbicides”, W. T. Thomson, 1986–87 Revision, Thomson Publications.

*Agricultural Chemicals* Book III, “Fumigants, Growth Regulators, Repellents, and Rodenticides”, W. T. Thomson, 1986 Revision, Thomson Publications.

*CRC Handbook of Natural Pesticides*, vol. III, “Insect Growth Regulators”, Parts A and B, E. David Morgen et al, CRC Press, including an introduction and index portion.

*Freshwater Vegetation Management*, Edward O. Gangstad, Thomas Publications, 1986.
*Flies of Public Health Importance*, CDC Training Guide, Insect Control Series, U.S. Department of Health, Education and Welfare, H. G. Scott et al, Apr. 1958.
*Guidelines for the Contol of Insect and Mite Pests of Foods, Fibers, Feeds, Ornamentals, Livestock, and Household*, U.S. Department of Agriculture, Agriculture Research Service, Agriculture Handbook No. 584, Jan. 1982.
*Scientific Guide to Pest Control Operations*, Second Edition (Revised), L.C. Truman et al, Purdue University, 1967.
*Aquatic and Wetland Plants of Florida*, D. P. Traver et al, Bureau of Aquatic Plant Research and Control, Florida Department of Natural Resources, 1978.
*Complete Guide to Pest Control—With and Without Chemicals*, G. W. Ware, Thomas Publications, 1980.
*Herbicide Handbook* of the Weed Science Society of America, Fifth Edition 1983.

*Technical Bulletin* relating to “Sonar®”, herbicide, Elan Co Products Company.

*Technical Bulletin* relating to “Scout™”, herbicide for broad spectrum aquatic weed control, Monsanto Company.

*Technical Bulletin* relating to “System L”, and System E, aquatic herbicides, 4–D Products, Inc.

(List continued on next page.)

*Primary Examiner*—Melvyn I. Marquis
*Assistant Examiner*—Robert H. Harrison
*Attorney, Agent, or Firm*—Richard E. Jenkins, P.A.

[57] ABSTRACT

Superabsorbent solid organic polymers which absorb over 100 times their weight in water are used in aquatic environment insect population control compositions. Methods for using the superabsorbent polymer insecticidal delivery agents for the control of aquatic environment insect populations, including mosquito population control methods, in an area needing aquatic environment insect population control treatment or in a dry area that is expected to need aquatic environment insect population control, are described.

14 Claims, No Drawings

U.S. PATENT DOCUMENTS

| | | |
|---|---|---|
| 3,415,614 | 12/1968 | Egan et al. . |
| 3,417,181 | 12/1968 | Cardarelli ............................ 424/409 X |
| 3,438,893 | 4/1969 | Anderson et al. ...................... 210/633 |
| 3,535,423 | 10/1970 | Ordas . |
| 3,576,760 | 4/1971 | Gould et al. . |
| 3,590,119 | 6/1971 | Cardarelli ................................ 424/409 |
| 3,661,815 | 5/1972 | Smith ................................. 525/54.32 |
| 3,755,064 | 8/1973 | Maierson .......................... 71/64.13 X |
| 3,857,934 | 12/1974 | Bernstein et al. ...................... 424/409 |
| 3,877,928 | 4/1975 | Houston et al. ......................... 504/116 |
| 3,900,378 | 8/1975 | Yen et al. ................................ 522/72 |
| 3,957,480 | 5/1976 | Kornis . |
| 3,973,355 | 8/1976 | McKenzie ............................... 521/905 |
| 3,980,463 | 9/1976 | Muramoto et al. .................... 504/116 |
| 4,007,258 | 2/1977 | Cohen et al. ........................... 424/409 |
| 4,053,627 | 10/1977 | Scher . |
| 4,058,124 | 11/1977 | Yen et al. .............................. 71/79 X |
| 4,070,348 | 1/1978 | Kraemer et al. . |
| 4,076,663 | 2/1978 | Masuda et al. ...................... 525/54.31 |
| 4,123,249 | 10/1978 | Vartiak et al. .......................... 504/152 |
| 4,123,381 | 10/1978 | Morishita et al. ........................ 502/62 |
| 4,131,648 | 12/1978 | Choi et al. ............................. 424/484 |
| 4,134,863 | 1/1979 | Fanta et al. . |
| 4,154,818 | 5/1979 | Kanada et al. . |
| 4,160,033 | 7/1979 | Garrett et al. .......................... 424/285 |
| 4,182,620 | 1/1980 | Denninger et al. . |
| 4,198,782 | 4/1980 | Kydonieus et al. ......................... 47/58 |
| 4,244,728 | 1/1981 | DelliColli et al. .......................... 71/65 |
| 4,244,729 | 1/1981 | DelliColli et al. .......................... 71/65 |
| 4,267,280 | 5/1981 | McCormick . |
| 4,277,364 | 7/1981 | Shasha et al. .......................... 424/488 |
| 4,304,591 | 12/1981 | Mueller et al. . |
| 4,307,115 | 12/1981 | Klopping ............................... 514/477 |
| 4,344,857 | 8/1982 | Shasha et al. . |
| 4,349,553 | 9/1982 | Brown . |
| 4,375,535 | 3/1983 | Kightlinger et al. ................... 527/313 |
| 4,389,513 | 6/1983 | Miyazaki ............................... 525/186 |
| 4,400,391 | 8/1983 | Connick, Jr. . |
| 4,401,456 | 8/1983 | Connick, Jr. . |
| 4,421,759 | 12/1983 | Boisvenue . |
| 4,497,930 | 2/1985 | Yamasaki et al. ...................... 524/556 |
| 4,500,338 | 2/1985 | Young et al. . |
| 4,540,427 | 9/1985 | Helbling .................................. 71/27 |
| 4,544,693 | 10/1985 | Surgant ................................. 524/375 |
| 4,639,366 | 1/1987 | Heller . |
| 4,640,044 | 2/1987 | Varnon . |
| 4,667,436 | 5/1987 | Benson . |
| 4,692,494 | 9/1987 | Sonenstein ............................... 525/57 |
| 4,707,359 | 11/1987 | McMullin ............................... 424/92 |
| 4,722,838 | 2/1988 | Tocker . |
| 4,725,628 | 2/1988 | Garvey et al. .......................... 521/905 |
| 4,725,629 | 2/1988 | Garvey et al. .......................... 521/905 |
| 4,731,391 | 3/1988 | Garvey et al. .......................... 521/905 |
| 4,743,448 | 5/1988 | Bahadir et al. ......................... 424/405 |
| 4,746,513 | 5/1988 | Smith .................................... 424/408 |
| 4,808,408 | 2/1989 | Baker et al. ............................ 424/408 |
| 4,818,534 | 4/1989 | Levy ..................................... 424/404 |
| 4,983,389 | 1/1991 | Levy ..................................... 424/404 |
| 4,983,390 | 1/1991 | Levy ..................................... 424/404 |
| 4,985,251 | 1/1991 | Levy ..................................... 424/404 |
| 5,037,654 | 8/1991 | Puritch et al. .......................... 424/405 |
| 5,080,226 | 1/1992 | Hodakowski et al. .................. 206/205 |

OTHER PUBLICATIONS

*Technical Bulletin* relating to "Agricultural Intermediates", emulsifiers, spray adjuvants, surfactants, dispersants, polymers for agricultural applications, Rohm Haas Company.

*Technical Bulletin*, relating to "Terra–Sorb", including MSDS on Terra–Sorb, Terra–Sorb AG, GB, HB, and 200G.

*Product Bulletin*, relating to "SANWET®", including MSDS on SANWET IM–1500, 1500P, 1500F and 1000.

CULIGEL ™ SP Superabsorbent Polymer Label and Research and Development Update: CULIGEL ™ SP Superabsorbent Polymer.

*Technical Bulletin* relating to "Hydrothol® 191," granular aquatic algaecide and herbicide, Pennwalt.

*Technical Bulletin* relating to "Komeen®", aquatic herbicide, Sandoz, Inc.

*Technical Bulletin* relating to "K–Tea" Algaecide, Cocide Chemical Corporation.

*Technical Bulletin* relating to "Morwet® EFW Powder", surfactant, DeSoto, Inc.

*Technical Bulletin* relating to "Poly Control 2 ", sticker and drift control agent for pesticides, JLB International, Inc.

*Technical Bulletin* relating to "Rhodia 2, 4–D Gran 20" herbicide, Rhone–Poulenc Chemical Company.

*Technical Bulletin* relating to "Revenge ™," systemic herbicide, Hopkins Agricultural Company.

*Technical Bulletin* relating to "Banvel® 720" herbicide, Velsicol Chemical Corp.

*Technical Bulletin* "Chem–trol ™," Spray Additive Deposition and Draft Retardant, Loveland Industries, Inc.

*Product Bulletin* relating to "Ortho Diquat Herbicide –H/A". Chevron Chemical Company.

*Technical Bulletin* relating to "Dissolvo ™ –45", a water soluble, heat sealable, stable pouching material, Gilbreth International Corp.

*Technical Bulletin* relating to "Fenoxycarb", insect growth regulator, Maag.

*Technical Bulletin* relating to "Ferro–Tech" agglomeration equipment, Ferro–Tech.

*Technical Bulletin* relating to "Hydout ™" aquatic weed killer, Pennwalt Corp.

*Technical Bulletin*, relating to "Cytrol® Amitrole–T," liquid weed killer.

*Technical Bulletin* relating to "Aquaathol® K", aquatic herbicide.

*Technical Bulletin* relating to "Casoron®, G–10" herbicide, aquatic weed control.

*Technical Bulletin* relating to "Cutrine® –plus." algaecide/herbicide.

*Technical Bulletin* relating to "A and V –70 granular", granulated algaecide.

*Technical Bulletin* relating to "Aquazine®" algaecide, for control of algae and certain pond weeds, Ciba–Geigy.

*Technical Bulletin* relating to "Aquastore®" Soil Additive, Cyanamid. Including MSDS on Aquastore® 1, 2, 3 Soil Water Retention Aid and Aquastore Absorbent Polymer.

*Material Safety Data Sheet*, "Super Sorb", Super Absorbent Company, Inc.

*Technical Data* relating to "Super Slurper" from U.S. Department of Agriculture.

*Technical Data* relating to "Water Lock®," including A–100 Series, G–100 Series, L–Series, and J–500 Series.

*Technical Data*, relating to "Aridall" including 1080, 1078, 1091, 1092, and 1098.

*Technical Bulletin*, relating to "Adjuvant List", State of Florida, Department of Natural Resousres.

*Report* relating to "Agrigel", Hazelton Raltech, Inc.

*Technical Bulletin*, relating to "Aquashade", Aquatic Plant Growth Control.

*Technical Bulletin*, relating to "Amine 6D" herbicide, Asgrow Florida Company.

Levy et al., "Effect of Water Quality on the Efficacy of Water–Base Suspensions of Arosurf® MSF Against Larvae of *Aedes taeiorhynchus*: Bioassay Evaluations," *Journal of the American Mosquito Control Association*, vol. 3, No. 6, pp. 631–641, Dec. 1987.

Klier et al., "Solute and Penetrant Diffusion in Swellable Polymers. VIII. Influence of the Swelling Interface Number on Solute Concentration Profiles and Release", *Journal of Controlled Release*, 7 (1988) 61–68.

Roorda et al., "Zero–Order Release of Oxprenolol–HCl, A New Approach", *Journal of Controlled Release*, 7 (1988) 45–52.

Kamal et al., "UPTAKE of $^{14}$C–Simetryn By Duckweed (lemna minor) During Release From A Polymer Matrix and the Consequent Herbicidal Effects", *Journal of Controlled Release*, 7 (1988) 39–44.

Wing et al., "Amylose Content of Starch Controls the Release of Encapsulated Bioactive Agents", *Journal of Controlled Release*, 7 (1988) 33–37.

Trimnell et al., "Autoencapsulation: A New Method for Entrapping Pesticides Within Starch", *Journal of Controlled Release*, 7 (1988) 25–31.

*Modern Mosquito Control*, 5th addition, Cyanamid.

Prodeedings of the 14th International Symposium on Controlled Release of Bioactive Materials (1987), Controlled Release Society, Inc., selected proceedings including pp. 158–167, 202–210, 244–252, 284–292 and 310, including a copy of the Table of Contents.

Program and Abstracts of 15th International Symposium on Controlled Release of Bioactive Materials, held in Basel, Switzerland, Aug. 15–19, 1988, including paper Nos. 15, 17, 19, 20, 23, 27, 30, 31, 55, 110, 130, 135, 139, 152, 170, 171, 173, 175, 190, 191, 195, 201, 204 and 262.

Levy et al., "Control of Immature Mosquitoes With a Single–, Joint–, or Multi–Action Polymer–Base Insecticide Delivery System," presented at the 15th International Symposium on Controlled Release of Bioactive Materials held in Basel, Switzerland, Aug. 15–19, 1988.

Levy et al., "Control of Immature Mosquitoes With a Single–, Joint–, or Multi–Action Polymer–base Insecticide Delivery System," presented at the 18th International Congress of Entomology, University of British Columbia, Vancouver, BC, Canada, July 3–9, 1988.

"Super Slurper", Mar. 1988, *Popular Science*, p. 9, article discloses the use of nematodes in combination with super slurper for use on citrus roots before planting to control weevils.

Hester, "Field Phytotoxicity Studies with Arosurf® MSF", Department of Health and Rehabilitative Services, West Florida Arthropod Research Laboratory.

Axtell et al., "Encapsulation of the Mosquito Fungal Pathogen *Lagenidium Giganteum* (OOMYCETES:LAGENIDIALES) in Calcium Alginate," *Journal of the American Mosquito Control Association*, vol. 3, No. 3, pp. 450–459, Sep. 1987.

O'Neill, "Membrane Systems", *Controlled Release Technologies*, Chapter 4, pp. 129–182.

Kydonieus, "Other Controlled Release Technologies and Application", *Controlled Release Technologies*, Chapter 13, pp. 235–257.

Thomson, "A Guide to Agricultural Spray Adjuvants Used in the United States", 1986 edition, including a copy of Table of Contents and selected pp. 50, 105, 107, 109, 111, 112, 154 and 155.

Levy et al., "Experimental Joint Action Formulations of Arosurf® MSF and *Bacillus Thuringiensis* Var. *Israelensis* or *Bacillus Sphaericus*", presented at 1987 AMCA meeting Seattle, Washington, Mar. 29 –Apr. 2.

Levy et al., "Laboratory Evaluations of Experimental Formulations of Arosurf® MSF and *Bacillus Thuringiensis* Var. *Israelensis, Bacillus Sphaericus* or Abate $^R$ 4–E," presented at 1987 FAMA meeting Palm Beach, Florida, May 31–Jun. 3.

Morrill, *Journal of the American Mosquito Control Association*, News and Notes, pp. 565–566, vol. 2, No. 4, Dec. 1986, cites a Newsweek article giving a brief mention to the possibility of "microsponges" for the release of insect repellents, including copy of Table of Contents.

Miller, "Dimensionally Stable Soluble Pouches for Safety", Pesticide Formulations and Application System, vol. 8, American Society for Testing and Materials, 1988.

*FRASS Newsletter*, vol. 8, No. 1, 1985, discloses a starch graft polymer (SGP) called "Super Slurper" for use in coating seeds, preventing soil erosion, fighting fires, and absorbing chemical spills.

"AROSURF® MSF," mosquito larvicide and pupicide, Technical Bulletin on this product as a mosquito control treatment.

*Technical Bulletin*, "TEKNAR®," larvicide for mosquito and blackfly control prepared from *Bacillus thuringiensis* berliner, var. israelensis.

*Technical Bulletin*, "VERTOBAC–G®," granular formulation of *Bacillus thuringiensis* formulated as granules with a carrier of corn cob particles.

"PYRENONE®, TOSSITS®," encapsulated larvicide.

"Bactimos Briguet," a sustained release mosquito control product.

Baines, "Biodegradation of Polyvinyl Alcohol" and Bryan et al., Biodegradation of Synthetic Warp Sizes.

Technical Bulletin, water soluble films, including "Quik Sol A and P," Edisol–m, EM–1100, QSA 2000 and Mono–Sol.

Leppla, "Gelling Agents for Insect Diet: From Mush to Medium", discussion of natural thickeners and their chemical structures.

"Altosid® Briquet, Product Application Bulletin", Technical Bulletin, No. 1115–81–2, Zoecon Corporation, formulation designed to time release insect growth regulator.

*Material Safety Data Sheet*, Grain Processing Corporation, Water Lock® Superabsorbent Polymer "G" Series.

*Data Sheet*, Super Absorbent Company , "Super Sorb".

*Material Safety Data Sheet* "Terra–Sorb".

*Material Safety Data Sheet* "Terra–Sorb GB".

*Product Data Sheet*, "Water Lock G–100 Superabsorbent Polymer", Grain Processing Corporation.

SGP®, "Safety of SGP® 502S Absorbent Polymer", Material Published from General Mills Chemical Inc.

Prichard et al., "Super Soil Moisturizer Challenges Others in Growing Industry" *Ornamentals South*, edited from a speech to the American Institute of Landscape Architects, Las Vegas, Nevada, Aug. 22, 1981.

Del Deterling, "Super Slurper Gets Your Crop Moving Earlier", *Progressive Farmer*, Feb. 1981.

Weaver et al., "A Practical Process for the Preparation of Super Slurper, a Starch Based Polymer With a Large Capacity to Absorb Water", *Die Starke* 29.Jahrg.1977/Nr. 12,S. 413–422.

"Super Slurper: Compound with a Super Thirst", Reprinted for *Agricultural Research*, Jun. 1975, Published by the U.S. Department of Agriculture.

Whitmore, "Transplant Survival Improved", *Christmas Trees*, vol. 10, No. 1, Jan. 1982.

Burgess et al., "A New Method for Applying Arosurf® MSF (Monomolecular Surface Film Formulations)", *Journal of American Mosquito Control Association*, vol. 1, No. 2, pp. 245–247, Jun. 1985.

Levy et al., "Effect of Low Temperature on the Mosquito Larvicide and Pupicide Arosurf® MSF (Monomolecular Surface Film) and Adol® 85 (Indicator Oil): Physical Evaluations", *Mosquito News*, vol. 44, No. 3, pp. 419–422, Sept. 1984.

Levy et al., "Florida Mosquito Control Districts Use Arosurf® 66–E2", *Pest Control*, Field Guide, Apr., 1983.

Levy et al., "Comparative Efficacy of Technical and Water–Base Formulations of Arosurf® MSF Against *Aedes Taeniarhynchus*", *Journal of American Mosquito Control Association*, vol. 2, No. 4, pp. 560–562, Dec. 1986.

Levy et al., "Laboratory Evaluations of Formulations of Arosurf® MSF and *Bacillus Sphaericus* Against Larvae and Pupae of *Culex Quinquefasciatus*", *Journal of American Mosquito Control Association*, vol. 2, No. 2, pp. 233–236, Jun. 1986.

Levy et al., "Control of Immature Mosquitoes Through Applied Surface Chemistry", *Proceedings of th Florida Anti–Mosquito Association*, vol. 51, No. 2, pp. 68–71.

Levy et al., "Investigations on the Mosquito Control Potential of Formulations of Arosurf® MSF and Conventional Larvicides", *Mosquito News*, vol. 44, No. 4, pp. 592–595, Dec. 1984.

Levy et al., "Efficacy of Arosurf® MSF (Monomolecular Surface Film) Base Formulations of *Bacillus Thuringiensis* Var. *Israelensis* Against the Mixed Populations of Mosquito Larvae and Pupae: Bioassay and Preliminary Field Evaluations", *Mosquito News*, vol. 44, No. 4, pp. 537–543, Dec. 1984.

Levy et al., "Additional Studies on the Use of the Monomolecular Surface Film Arosurf® 66–E–2 for Operational Control of Mosquito Larvae an Pupae", *Journal of Florida Anti–Mosquito Association*, vol. 53, No. 2, pp. 100–106, 1982.

Hertlein et al., "An Injection Method for Spraying Biological Control Agents and a Monomolecular Surface Film for Control of Immmature Mosquitoes", *Journal of American Mosquito Control Association*, vol. 1, No. 2, pp. 255–257, June 1985.

Levy et al., "Efficacy of the Organic Surface Film Isostearyl Alcohol Containing Two Oxyethylene Groups for Control of *Culex* and *Psorophora*, Mosquitoes: Laboratory and Field Studies", *Mosquito News*, vol. 42, No. 1, pp. 1–11, Mar. 1982.

Levy et al., "Control of Larvae and Pupae of *Anpoheles Quadrimaculatus* and *Anopheles Crucians* in Natural Paludal Ponds With The Monomolecular Surface Film Isostearyl Alcohol Containing Two Oxyethylene Groups", *Mosquito News*, vol. 42, No. 2, pp. 172–178, Jun. 1982.

Levy et al., "Ground and Aerial Application of a Monomolecular Organic Surface Film to Control Salt–Marsh Mosquitoes in Natural Habitats of Southwestern Florida", *Mosquito News*, vol. 41, No. 2, pp. 291–301, Jun. 1981.

Levy et al., "Persistence of the Mosquito Larvicide and Pupicide Arosurf® MSF in Permanent and Semi–Permanent Habitats", *Journal of Florida Anti–Mosquito Association*, vol. 56, No. 1, pp. 32–36, 1985.

Levy et al., "Formulations for Enhancing the Mosquito Larvicidal Action and Persistence of the Monomolecular Surface Film Isostearyl Alcohol Containing Two Oxyethylene Groups (Aro–surf® MSF", *Journal of Florida Anti–Mosquito Association*, vol. 55, No. 1, pp. 31–34, 1984.

Harwood et al., Entomology In Human and Animal Health, Seventh Edition, 1979, Macmillan Publishing Co., Inc., New York, NY, title page and table of contents.

Agis F. Kydonieus, *Controlled Release Technologies: Methods, Theory, and Applications*, vols. I and II, 1980, CRC Press, Inc., Boco Raton, Florida, and specifically pp. 1 through 19 and 116 through 127 of vol. I, which relate to information on controlled release in general and specifically to herbicides; pp. 240 through 246 of vol. I, which relate to controlled from ultramicroporous triacetate; vol. II, pp. 241 through 257, which relate to controlled release from gels including a list of cited patent literature; and pp. 8 through 62 of vol. II, which relate to the biodegradative controlled release of pesticides from polymeric substrates, as well as a copy of the detailed Table of Contents.

Richard Baker, *Controlled Release Technologies of Biologically Active Agents*, 1987, John Wiley & Sons, New York, NY, pp. 177–191, as well as the detailed Table of Contents.

Levy et al., "Control of Immature Mosquitoes With Liquid and Solid Formulations of a Monomolecular Organic Surface Film", presented at the Joint Meeting of the American Mosquito Control Association and California Mosquito and Vector Control Association, Apr. 18–22, 1982, Sacramento, California, pp. 106–108.

Kertesz, J. A., et al., "Field Trials of Arosurf MSF alone and in combination with Bti for Mosquito Control", Publisher: New Jersey Mosquito Control Association, Inc., Meeting Info.: Proceedings, 72nd Annual Meeting, New Jersey Mosquito Control Association, Inc., Atlantic City, New Jersey, 17–21 March 1985, pp. 167–168.(Conference Article, Abstract Provided).

५,८२४,३२८

INSECTICIDAL DELIVERY COMPOSITIONS AND METHODS FOR CONTROLLING A POPULATION OF INSECTS IN AN AQUATIC ENVIRONMENT

This is a continuation of application Ser. No. 07/560,286, now abandoned filed on Jul. 30, 1990, which is a continuation of U.S. Ser. No. 07/211,895, filed Jun. 27, 1988, now abandoned, which is a divisional of U.S. Ser. No. 07/032,532, filed Apr. 1, 1987, now U.S. Pat. No. 4,818,534.

BACKGROUND AND SUMMARY OF THE INVENTION

1. Field of the Invention

The present invention relates to an insecticidal delivery composition made from one or more solid superabsorbent polymers with or without one or more liquid or solid insecticidal or noninsecticidal film-forming or surface active agents, ovicides, larvicides, pupicides, insecticides, biological control agents, pathogens, parasites, microbial control agents, insect growth regulators, conventional toxicants, pesticides, or other additives. The present invention also relates to a method of applying the insecticidal delivery composition alone or with one or more active insecticidal ingredients to an aquatic environment having a natural population of aquatic environment insects, for the purpose of controlling that population of insects. The present invention also relates to the use of the insecticidal delivery composition for a pretreatment application to an aquatic insect dry habitat in order to control that population of aquatic insects that will breed when the insect habitat becomes flooded by rain or tides. This invention further relates to a facile method of combining two or more active insecticidal ingredients, one of which is a film-forming agent, on a superabsorbent insecticidal delivery composition for ground or aerial application. This manner of application makes possible the mixing of active insecticidal ingredients that would otherwise be difficult or substantially impossible to combine as a joint or multiple action formulations for spray application.

2. General Background

In particular, the present invention is directed against mosquitoes that breed in permanent or semipermanent, natural or artificial, aquatic habitats. Mosquitoes of major importance to be controlled by the present invention are species of the genera of Aedes, Anopheles, Culex, Culiseta, Coquillettidia, Deinocerites, Mansonia, Psorophora, Uranotaenia, and Wyeomyia. It is the main objective of this invention to direct the use of the insecticidal delivery composition for the control of the immature aquatic stages of various species of mosquitoes before they become biting adults capable of being a nuisance and/or transmitting a disease. This technique is cost-effective and reduces the environmental and health hazards that can result when insecticides are extensively broadcast over large areas for the control of the adult stages.

In addition to mosquitoes, other species of aquatic environment insects such as biting and nonbiting midges, black flies, moth flies, crane flies, horse flies, deer flies, hover or flower flies can constitute a nuisance and often a health threat to humans and livestock. Thus, their growth as a population, if unchecked, can be detrimental. The medical and veterinary importance of various species of mosquitoes and other important aquatic environment insects are discussed in detail by Robert F. Harwood and Maurice T. James in "Entomology In Human and Animal Health," Seventh Edition, 1979, MacMillan Publishing Co., Inc., New York, N.Y., which is incorporated herein by reference. Therefore, the scope of the present invention also relates to the use of the insecticidal delivery composition with one or more active insecticidal ingredients for controlling various species of aquatic environment insects other than mosquitoes.

Compositions and methods for controlling and killing insects are well known. A number of patents discuss the use of pesticides or insecticides. U.S. Pat. No. 3,535,423 discloses a wettable powder pesticide concentrate that may be dispersed in water. This is described as allowing the otherwise insoluble pesticide to become soluble in water. U.S. Pat. No. 4,267,280 discloses controlled release pesticides and their preparation. These pesticides are described as polymers with a macro-molecular backbone and pendant groups having pesticidal groups chemically linked thereto and prepared by reacting a pesticide having a replaceable hydrogen with a multifunctional isocyanate to form an adduct which is then reacted with a polyol polymer substrate. U.S. Pat. Nos. 4,400,391 and 4,401,456 disclose the use of alginate gel beads to encapsulate bioactive materials to provide for their controlled release. The patents describe beads being made to either float or sink and they may contain insecticides. These beads are also described as acting as carriers to place the bioactive material near the target species, for example, a floating bead containing a herbicide releasing the herbicide in close proximity to floating aquatic weeds or the beads falling through foliage to release herbicide into the soil. U.S. Pat. No. 4,344,857 contains a disclosure that is similar to those immediately above; however it involves encapsulation by xanthate derivatives and does not disclose the ability to be used in conjunction with an aqueous environment.

A number of patents describe the use of substances other than pesticides to control the growth of insects. U.S. Pat. No. 4,053,627 discloses a controlled release system for juvenile hormones in aqueous environments. This is described as being accomplished with alginate gel discs comprising alginate, a solubilizing agent, and a salt which yields cations, and containing the juvenile hormone. U.S. Pat. No. 4,160,033 discloses a method for the control of mosquitoes by the use of film-forming materials. The method is disclosed as involving the use of a film of organic material which reduces the surface tension of the body of water, and subsequently causes the mosquito larvae and pupae to drown.

At the present time, application of film-forming agents for mosquito control is essentially limited to liquids. Easier and more efficient ground and aerial delivery techniques are proposed by utilizing the film-forming insecticidal delivery composition as dusts, pellets, granules, or briquets that can float or sink. See, for example, Levy et al, "Control of Immature Mosquitoes With Liquid and Solid Formulations of A Monomolecular Organic Surface Film", Proceedings and Papers of the Fiftieth Annual Conference of the California Mosquito and Vector Control Association, Inc., and the Thirty-Eighth Annual Meeting of the American Mosquito Control Association, Apr. 18–22, 1982, Sacramento, Calif., pp. 106–108.

Technical film-forming agents applied as conventional liquid sprays cannot penetrate dense vegetation at low application rates. Therefore, most of the costly insecticidal film-forming agent impinges on the vegetation and does not reach the water where the mosquitoes are breeding. In addition, the use of water as a diluent for application of large volumes for easier vegetative penetration without overdosing requires high speed agitation or the use of water injection systems to adequately suspend the film-forming agent in the water for accurate application rates. Formulation of at least one film-forming agent with superabsorbent polymer(s) of the present invention into an agglomerated solid, e.g., a dense pellet or granule, allows penetration through the vegetative canopy for release of the film-forming agent into the target aquatic habitat without the costly overdosing or mixing problems that can occur with liquid sprays. At present, liquid film-forming agents used for mosquito control are applied to the water surface only. Since the film-forming agent floats because of its specific gravity, it can be adversely affected or removed from the target habitat by drying, runoff, drainage, or constant wind fetch. Superabsorbent-based film-forming agent compositions of the present invention can be formulated to sink or float. Sinking formulations as granules could be evenly distributed over the habitat at the desired dosage and would slowly release film-forming agent to the water surface where it can control immature mosquitoes without being as severely affected by inhibiting pressures such as runoff or wind fetch. In addition, formulations of superabsorbent polymer(s) and a film-forming agent of the present invention can effect a mechanism for slow or controlled release, thereby extending the field life or persistence of the surface film for a greater period of time than would be expected with a liquid film-forming agent. Certain superabsorbent polymer formulations of the present invention are expected to extend the field persistence of the liquid formulations and thereby assure that the number of costly insecticide treatments per habitat will be significantly reduced.

None of the prior art methods or compositions for controlling insect populations are without disadvantages. One major problem associated with many of the aforementioned compositions and methods of the prior art is their inability to simultaneously apply immiscible, or otherwise incompatible substances to the area to be treated. It has been found that while film-forming materials, when combined with diluents, ovicides, larvicides, pupicides, insecticides, pesticides, conventional toxicants, biological control agents, microbial control agents, pathogens, parasites, or insect growth regulators, may produce improved insect controlling efficacy over single active component formulations, problems with mixing the ingredients often result. Blends of Arosurf® MSF (a film-forming agent) and water or technical and/or water-base blends of Arosurf® MSF and various formulations of *Bacillus thuringiensis* var. *israelensis* (*B.t.i.*), or *Bacillus sphaericus* or Abate® 4-E do not form homogeneous suspensions when casually mixed, and therefore required frequent and vigorous agitation. When allowed to stand, the components would separate into distinct phases because of the differences in their respective specific gravities, and/or the presence of incompatible inert formulation ingredients, and therefore these joint action formulations would require either a continuous agitation or a reagitation to effectively remix the components just prior to their application.

These mixing and remixing requirements make it very difficult to apply these liquid formulations by conventional means. To circumvent some of these problems, high pressure water injection systems have been developed. But, high pressure water injection requires high volumes of water to deliver the formulation. This, among other structural limitations, renders application of certain single, joint or multiple action formulations for insect population control difficult by helicopter. Helicopter application is often a must for both economic efficiency and because many aquatic environment insect breeding areas are not otherwise accessible.

While it may be possible to incorporate some known components, singly or jointly or multiply into a solid agglomerated matrix, these formulations have been found to lack the quick or controlled release ability and the ability to control both mosquito larvae and pupae simultaneously while effectively and spontaneously spreading the active ingredients over the target habitat.

Since other solid agglomerated insecticidal compositions do not have rapid self-spreading characteristics, they require even applications to assure that the active insecticidal ingredient(s) are uniformly dispersed in the aquatic habitat to assure effective control of the target insects that may be widely dispersed in the habitat. In addition, the other solid agglomerated insecticidal components usually affect only one immature developmental stage. The use of insecticidal delivery compositions made from one or more superabsorbent polymers of the present invention with a pupicidal film-forming agent (e.g., Arosurf® MSF) and larvicidal agent such as *B.t.i.* or *Bacillus sphaericus* have self-spreading potential and can kill mosquito larvae, pupae, or emerging adults rapidly in areas far removed from the initial points of application. Although Arosurf® MSF can kill mosquito larvae and pupae, their impact on larval populations is usually very slow.

No single or joint action solid agglomerated formulations are available that claim rapid larvicidal and pupicidal action and self-spreading characteristics. Commercial solid agglomerated formulations of *Bacillus thuringienesis* var. *israelensis*/(Vectobac® G, Teknar® granules, Bactimos® briquets, Bactimos® granules or pellets), Abate® (1-SG, 2-CG, 5-CG), Dursban® 10CR, Furadan® 3, or Furadan 5 granules, and Altosid® briquets are available that have slow or quick immature stage kill potential, and/or fast or slow release characteristics; however, these do not have rapid multidevelopmental stage control potential, do not have self-spreading characteristics, are typically composed of only one active insecticidal ingredient that cannot be simply and rapidly detected or monitored under field conditions by insecticide applicators, and are composed of non-superabsorbent polymer materials. For example, the Altosid® briquet is an insect growth regulator formulation designed to sink and release effective levels of the chemical for approximately 30 days. Altosid® is released as the charcoal-like briquet erodes. Treated larvae continue to develop normally to the pupal stage where they die. Bactimos® briquets are composed of cork-like matrices that float and release effective levels of *B.t.i.* for approximately 30 days where they kill mosquitoes only in the larval stage. In addition, most of the products mentioned will not kill late 4th instar mosquito larvae and, with the exception of Altosid® which kills the mosquito slowly when it reaches the pupal stage, none of the products will directly kill pupae or emerging adults.

The active ingredients of the aforementioned products in their standard formulations can be formulated on a superabsorbent polymer of the present invention to provide an alternate substrate (carrier), or more preferably can be formulated with one or more larvicidal/pupicidal film-forming agents such as Arosurf® MSF to provide a joint action formulation that kills larvae, pupae, or emerging adults rapidly, has spontaneous spreading ability for better distribution of the active ingredients throughout the target habitat, and has the ability to be chemically monitored in the target habitat to determine the presence or persistence of one or more active insecticidal components.

Compaction of the superabsorbent polymer matrix of the present invention has been shown to effect a slow-release mechanism for certain active ingredients. In addition, varying the ratio of different types of these superabsorbent polymers of the present invention that have differential water uptake characteristics (e.g., Water Lock® products) in a single compacted or agglomerated matrix may effect a mechanism to further enhance the slow-release of certain active insecticidal ingredients. In addition, the varying specific gravities (i.e., less than or greater than one) of the superabsorbent polymers of the present invention can be used to develop floating or sinking formulations for use in a variety of habitats to kill a variety of aquatic insect species.

Attempts have been made to incorporate film-forming agents such as those described in U.S. Pat. No. 4,160,033 on or in a variety of floating or submerged solid water soluble, erodible, and porous matrices such as sponges, reticulated polyurethane foam, agar, gelatin capsules, cork, vermiculite, zein, corn cob grits, charcoals, sand, clays, lignins, celite, wood chips, sawdust, cetyl or stearyl alcohols, and cellulose acetate or triacetates. However, these attempts have been unsuccessful because the combined matrix and film-forming agent was either too soft to handle and apply by conventional techniques, too hard to release a sufficient amount of the active film-forming agent for effective mosquito control, and/or the matrix could not be impregnated with a sufficient amount of the film-forming agent to permit application of the bulk material at rates that were practical for operational mosquito control.

Specific Objects

It is therefore an object of the present invention to provide compositions and methods for the pretreated dry habitat control and aquatic control of a population of aquatic environment insects, particularly mosquitoes, which overcome the problems and deficiencies of the prior art.

It is also an object of the present invention to provide a composition and method which is easy to prepare (formulate) and use (apply), and which is erodible (biodegradable) and safe to the environment, but which is effective for use in controlling one or more immature stages of natural population of aquatic environment insects, particularly mosquitoes.

It is further an object of the present invention to provide a composition and method which can incorporate a wide variety of ingredients into a single insecticidal delivery system to control a broad spectrum of aquatic environment insect populations, particularly mosquitoes, and to provide for the variable time release of those ingredients.

Still another object of the present invention is to provide a method for controlling natural populations of those species of mosquitoes that breed in small collections of water in tree holes, cans, birdbaths, tires, bromeliads, and other types of natural and artificial water holding containers, which only require the use of a material that is independently effective for the control of immature stages of certain species of mosquitoes.

These and other objects are accomplished by the compositions and methods of the present invention.

Specific Aspects

In accordance with one aspect of the present invention, there is provided an insecticidal delivery composition for controlling a population of aquatic environment insects, the delivery composition being applied as a pretreatment before the target habitat is flooded or as a direct treatment to the aquatic habitat. The composition includes at least one superabsorbent polymer, and at least one insecticidal agent, alone or in combination with a diluent or surface active agent, the polymer and insecticidal agent being present in a total amount effective to control the population of aquatic environment insects. The diluent or surface active agent if present, is at a concentration adapted to allow impregnation of the insecticidal agent(s) on the polymer(s).

In accordance with another aspect of the present invention, there is provided an insecticidal delivery composition for controlling a population of aquatic environment insects which includes at least one superabsorbent polymer, and at least one different insecticidal agent which is a film-forming agent, the polymer and agent being present in a total amount effective to control the population of aquatic environment insects, the delivery composition being applied as a pretreatment before the target habitat is flooded or as a direct treatment to the aquatic habitat.

In accordance with yet another aspect of the present invention, there is provided an insecticidal delivery composition for controlling a population of aquatic environment insects. The composition includes at least one superabsorbent polymer, at least one different insecticidal agent which is a film-forming agent, and at least one additional compound. The additional compound is selected from larvicides; pupicides; ovicides; insecticides; toxicants; pesticides; biological control agents; microbial control agents; pathogens; parasites; insect growth regulators; diluents; surface active agents, and mixtures thereof. The polymer, agent and additional compound are present in a total amount effective to control the population of aquatic environment insects, the delivery composition being applied as a pretreatment before the target habitat is flooded or as a direct treatment to the aquatic habitat.

In accordance with still another aspect of the present invention, there is provided a method for controlling a population of mosquitoes that breed in small water collections, e.g., container, tree hole, bromeliad, etc. The method includes the steps of:

- preparing or formulating an insecticidal delivery composition which includes at least one superabsorbent polymer; and;
- applying said insecticidal delivery composition in an amount effective to control the population of small water collection-breeding mosquitoes to an aquatic environment area needing control of the immature stages of these species of mosquitoes, the delivery composition being applied as a pretreatment before the target habitat is flooded or as a direct treatment to the artificial or natural aquatic habitat.

In accordance with another aspect of the present invention, there is provided a method for controlling a population of aquatic environment insects which includes the steps of:

- preparing an insecticidal delivery composition which includes at least one superabsorbent polymer and at least one insecticidal agent which includes a film-forming agent, by a series of soakings, washes, variable speed blending, and/or heat and moisture conditioning treatments;
- applying said insecticidal delivery composition in an amount effective to control the population of aquatic environment insects, to an aquatic area needing aquatic insect control treatment, the delivery composition being applied as a pretreatment before the target habitat is flooded or as a direct treatment to the aquatic habitat.

In accordance with still another aspect of the present invention, there is provided a method for controlling a population of aquatic insects. The method includes the steps of:

- preparing an insecticidal delivery composition which includes at least one superabsorbent polymer and at least one insecticidal agent which includes a film-forming agent and at least one additional compound. The additional compound is selected from ovicides; larvicides; pupicides; insecticides; conventional toxicants; pesticides; biological control agents, microbial control agents; pathogens; parasites; insect growth regulators; diluents; surface active agents; and mixtures thereof; and applying said insecticidal delivery composition in an amount effective to control the population of aquatic environment insects, to an aquatic environment needing aquatic insect control treatment, with the delivery composition being applied as a pretreatment before the target habitat is flooded or as a direct treatment to the aquatic habitat.

The superabsorbent polymers of the present invention are synthetic organic polymers which are solid and hydrophilic, absorbing over 100 times their weight in water. Generally, these superabsorbent polymers are chosen from acrylamide and acrylate polymers, co-polymers and terpolymers. These superabsorbent polymers are typically in a powder or flake form, adapted to be blended and/or agglomerated.

The acrylamide and acrylate superabsorbent polymers may be, for example, acrylamide alkali metal acrylate copolymers; propenenitrile homopolymers, hydrolyzed, alkali metal salts; polymers of propenamide and propenoic acid, alkali metal salts; hydrolyzed acrylonitrile copolymers, and starch graft copolymers and terpolymers thereof. All of these are designed to be hydrophilic, absorbing over 100 times their weight in water.

The present invention has been found to be particularly effective in controlling natural populations of mosquito species such as *Aedes taeniorhynchus, Aedes aegypti, Aedes albopictus, Aedes triseriatus, Culex quinquefasciatus, Culex nigripalpus, Wyeomyia mitchellii,* and *Wyeomyia vanduzeei* in an aquatic environment area needing mosquito control treatment.

Specific Advantages

The present invention provides numerous advantages over prior compositions and methods. For example, the methods of the present invention require that as little as one component be used to control the population of aquatic environment insects such as mosquitoes. The formulations of the present invention may be composed of a wide choice of either nontoxic or toxic biological or microbial control agents, pathogens, parasites, insect growth regulators, monomolecular surface films, larvicides, ovicides, pupicides, and/or conventional insecticides depending on the type or nature of the habitat to be controlled, the environmental impact, and/or the type of aquatic developmental stage or insect species to be controlled. The formulations of the present invention are biodegradable. They are also storage stable, basically as stable as the individual components; however, increased stability may occur in matrix form. The present invention can take a wide variety of shapes and forms which may be required for a particular application. The formulations of the present invention can have a variable time release, either quick, or gradual as the situation requires. The present invention provides a carrier for the delivery of joint or multiple active formulations of otherwise incompatible liquid or powdered insecticidal agents without the necessity of costly and complex agitation/application equipment. The present invention can be used as a pretreatment application to areas that are dry but are known to breed when flooded, thereby assuring that the first broods will be controlled. One or more of the carrier polymers without an added larvicidal or pupicidal ingredient can control immature stages of mosquitoes that breed in containers, tires, birdbaths, bromeliads, or other small water-holding receptacles by physical (nontoxic) mechanisms. The present invention is also not restricted to applications to any one type of aquatic environment.

Other objects, aspects and advantages of the present invention will be apparent to one of ordinary skill in the art from the following:

DESCRIPTION OF THE PREFERRED EMBODIMENTS

Surprisingly it has been found that certain superabsorbent polymers constitute a novel class of chemicals useful as insecticidal delivery compositions for controlling a population of insects in an aquatic environment area needing aquatic environment insect control treatment.

An insecticidal delivery composition is any composition which can carry, or be adapted to carry, insecticidal agent(s), biologically active or biologically inactive agent(s), etc., to the target habitat, natural or artificial, aquatic or dry. In a preferred embodiment, the insecticidal delivery agent is one or more superabsorbent polymers. Superabsorbent polymers, including starch graft copolymers, are well known in the art. See, for example, those described in U.S. Pat. Nos. 4,375,535 and 4,497,930 (incorporated herein by reference) which have had uses for adhesives, flocculants, sizers, water-retaining materials for agriculture and water-absorbing materials for sanitary materials. However, the advantages attendant the use of superabsorbent polymers as an insecticidal delivery composition and more specifically for mosquito control in an aquatic environment, have gone completely unrecognized.

The superabsorbent polymers of the present invention are synthetic organic polymers which are solid and hydrophilic, absorbing over 100 times their weight in water. Generally, these superabsorbent polymers are chosen from acrylamide and acrylate polymers, copolymers and terpolymers. These superabsorbent polymers are typically in a powder or flake form, adapted to be blended and/or agglomerated.

The acrylamide and acrylate superabsorbent polymers may be, for example, acrylamide alkali metal acrylate copolymers; propenenitrile homopolymers, hydrolyzed, alkali metal salts; polymers of propenamide and propenoic acid, alkali metal salts; hydrolyzed acrylonitrile copolymers, and starch graft copolymers and terpolymers thereof. All of these are designed to be hydrophilic, absorbing over 100 times their weight in water. The resulting hydrophilic polymers can absorb from over one hundred to greater than about 5000, more typically over 500 to about 1,000, times their own weight in water (measured using distilled water, pH 7.5, 25° C., 760 mm Hg., absorbtion within about 30 seconds). However, the absorbtion or swelling capacity and absorbtion or swelling time typically varies with each specific superabsorbent polymer.

One class of superabsorbent polymers include combinations of a starch and organic monomers, oligomers, polymers, copolymers or terpolymers. They may be manufactured in a variety of ways, for example the methods described in U.S. Pat. Nos. 4,375,535 and 4,497,930, and can be, for example, the product of grafting corn starch (amylopectin) with acrylonitrile (an acrylic monomer or oligomer).

The superabsorbent polymers can also be propenoic or acrylonitrile/acrylamide-base polymers or copolymers or terpolymers that also show superabsorbency properties.

It has also been observed that superabsorbent polymers alone, or impregnated with one or more insecticidal agent(s), have the ability to swell in water and release the substance(s) impregnated. Superabsorbent polymers also have the ability under certain conditions to reform or contract to a congealed consistency similar to their original form when evaporation has caused the water to be removed from the gel-like matrix, and then swell or re-gel when additional water is added. This ability to be functional after repetitive periods of wetting and drying is advantageous for pretreatment and/or prolonged control release applications.

Non-limiting specific examples of superabsorbent polymers with differential swelling properties, and which are particularly useful as insecticidal delivery agents include:

1) a copolymer of acrylamide sodium acrylate (Terra-Sorb™ GB);
2) hydrolyzed starch-polyacrylonitrile (Terra-Sorb™);
3) 2-propenenitrile, homopolymer, hydrolyzed, sodium salt or poly(acrylamide-co-sodium acrylate) or poly(2-propenamide-co-2-propenoic acid, sodium salt), (Water Lock® Superabsorbent Polymer G-100),
4) starch-g-poly(2-propenamide-co-2-propenoic acid, sodium salt), (Water Lock® Superabsorbent Polymer A-100);
5) starch-g-poly(2-propenamide-co-2-propenoic acid, sodium salt), (Water Lock® Superabsorbent Polymer A-200);
6) starch-g-poly(2-propenamide-co-2-propenoic acid, potassium salt), (Water Lock® Superabsorbent Polymer B-204);
7) poly(2-propenamide-co-2-propenoic acid, sodium salt), (Water Lock® Superabsorbent Polymer G-400);
8) poly-2-propenoic acid, sodium salt (Water Lock® Superabsorbent Polymer J-500);
9) starch-g-poly(acrylonitrile) or starch-g-poly (acrylamide-co-sodium acrylate), (General Mills® SGP 502s); and
10) starch acrylonitrile copolymer (Super Sorb/AG Sorbent).

Superabsorbent polymers are generally nontoxic, biodegradable, and relatively inexpensive to buy or produce.

It has further been observed that the insecticidal delivery agent consistent with a more preferred embodiment of the present invention, exhibit physical (nontoxic) insecticidal agent properties when applied to selected habitats that contain certain species of mosquitoes that breed in cans, birdbaths, tires, bromeliads, and other types of natural or artificial water holding containers, even without the presence of an additional insecticidal agent.

Thus, these superabsorbent polymers can be used in pretreatment or aquatic situations, independently, for controlling natural populations of mosquito species such as *Aedes aegypti, Aedes albopictus, Aedes triseriatus, Culex quinquefasciatus, Culex nigripalpus, Wyeomyia mitchellii,* and *Wyeomyia vanduzeei* in an aquatic environment area needing mosquito control treatment.

An insecticidal agent of the present invention is a compound which is effective in controlling a population of aquatic environment insects in an aquatic area needing aquatic insect control treatment. In a preferred embodiment, insecticidal agents include film-forming agents, ovicides, larvicides, pupicides, pesticides, insecticides, toxicants, biological control agents, pathogens, parasites, microbial control agents, and insect growth regulators. These insecticidal agents can be used alone or in combination; however, in a more preferred embodiment, the insecticidal agent contains at least one film-forming agent. As noted above, the preferred group of carriers exhibits physical (nontoxic) mosquitocidal agent properties. This is to say that the carriers are effective in controlling a population of certain species of mosquitoes that breed in small natural or artificial water collections.

Film-forming agents that are mosquitocidal are generally water-immiscible organic chemicals which form a film on water. The chemicals are generally nonionic, nonvolatile and water immiscible liquids. They may have a low freezing point, a boiling point above the maximum air temperature of the environment into which they are placed, and are capable of rapid and spontaneous spreading with high respreading potentials.

Examples of liquid, semisolid, or solid film-forming or surface active agents useful in conjunction with the present invention for insecticidal and/or noninsecticidal purposes are: the organic chemicals described in U.S. Pat. No. 4,160,033, which is herein incorporated by reference; and organic chemicals that reduce the water surface tension to greater than 31 dynes/cm and/or have an HLB No. greater than 10. Film-forming or surface-active agents such as 2-propanol, tridecyl alcohol, 2-ethyl butanol, 2-ethyl hexanol, 1-hexanol, acetone, xylene, decyl alcohol, polyoxyethylene (20) sorbitan trioleate, polyoxyethylene alkyl aryl ether, polyoxyethylene (5) sorbitan monooleate, isostearyl alcohol containing 10 oxyethylene groups, Morwet® surfactants, isostearyl alcohol containing 20 oxyethylene groups; or surface active petroleum-base oils such as mineral oils, diesel oils, etc., may be used. In addition, the insecticidal agents, and hence the insecticidal delivery compositions, may contain other types of ingredients such as diluents, enhancers, and/or binders, such as clays, gums, water, cetyl or stearyl alcohol.

HLB stands for "Hydrophile-Lipophile Balance", as defined in THE ATLAS HLB SYSTEM, Atlas Chemical Industries, Inc. (4th printing), 1963. The HLB number is an indication of the percentage of the hydrophilic portion of the nonionic emulsifier molecule, as defined on pages 3 and 18 of this reference.

A pupicide is any material that can kill that specific developmental stage of certain aquatic insects called a pupa. Pupicides are usually chemicals that kill pupae directly by forming petroleum or nonpetroleum films on the surface of water that cause the pupae to drown. This stage is nonfeeding and directly precedes the adult stage. Examples of pupicides useful in accordance with the present invention include Golden Bear oils such as GB-1111 or GB-1356, Arosurf® MSF, Flit MLO®, and Diesel oil or mineral oil base formulations. Biological/microbial pupal, control agents such as bacteria, fungi, protozoa, viruses, rickettsiae and nematodes may also be used.

A larvicide is any material that can kill that specific developmental stage of certain aquatic insects called a larva. Larvicides can kill larvae after ingestion of a toxic material, kill on or after contact with the integument, or kill by physical (nontoxic) and/or toxic means by causing the larvae to drown. The larval stage is a feeding stage that usually has several molting or growth phases called instars. For example, in mosquitoes there are four larval instars. The larval stage directly precedes the pupal stage. Examples of larvicides useful in accordance with the present invention include biological control agents or microbial control agents such as *Bacillus thuringiensis* var. *israelensis* (Vectobac®, Bactimos®, Teknar® Skeetal®) or *Bacillus sphaericus* (BSP-1); conventional toxicants such as Abate®, Baytex®, Dursban®, resmethrin, malathion, pyrethrins, allethrin, Baygon®, Furadan®, methoxychlor, etc.; and petroleum or nonpetroleum film-forming oils such as Flit MLO®, GB-1111 or GB-1356, and Arosurf® MSF. Other bacteria, fungi, protozoa, viruses, rickettsiae and nematodes may also be used.

Insect growth regulators (IGRs) are chemicals such as juvenile hormone or anti-juvenile hormone analogues that kill the target aquatic environment insect in one or more immature stages by adversely affecting the molting or developmental cycle. IGRs are not considered to be direct larvicides or pupicides. For the most part, larvae that are exposed to the chemical continue to develop normally until they reach the pupal stage where they die. Examples of IGRs are Aktosid®, Dimilin®, and fenoxycarb.

Insect population is used here to refer to one or more groups or species of aquatic environment insects that breed in any type of aquatic environment or habitat requiring control treatment. The population as used herein denotes a natural or artificial breeding area and the like or the aquatic insects, pupae, larvae and eggs contained within any geographical area needing aquatic environment insect control treatment. For example, a field, yard, pasture, pot hole, salt marsh, ditch, tire, woods, lake, stream, river, bay, pond, etc., may be treated. Of course, the area needing aquatic environment insect control treatment can be any size and the present invention is only limited by the amount of time, equipment, and material available.

Impregnation of superabsorbent polymers with fatty alcohol film-forming agents such as Arosurf® MSF or sorbitan monooleate appears to delay or slow down the rate of water absorption of superabsorbent polymers such as Super Sorb or Water Lock® G-100, thereby providing another useful mechanism for slow or controlled release of insecticidal agents in the aquatic environment. The slow or controlled release process could be further modified or delayed by the degree of compaction of the powdered or flaked superabsorbent polymer and superabsorbent polymer/insecticidal agent formulations, by varying the size of an orifice in a container into which the insecticidal delivery composition is placed, by varying the concentration of film-forming agent, by varying the concentration of different types of superabsorbent polymers, and by adding one or more binders. When used in small water collections to control certain species of mosquitoes, it appears that water that is held within the cross-linked gel-like superabsorbent polymer matrix evaporates slower when compared to a equivalent amount of free-standing water. In addition, the addition of certain film-forming agents to the polymer(s) also appears to retard the rate of water loss. These observations indicate that water in these small breeding receptacles will be physically inactivated (i.e. gelled) for longer periods of time, thus providing a habitat that is not suitable for mosquito breeding. These observations further suggest additional field persistence mechanisms of any active insecticidal ingredients which are added to the polymer matrix.

It should be noted that certain salts (e.g., alkali metal halides such as NaCl) have been shown to break the cross-linking of the superabsorbent polymer's matrix when introduced to water. This can have an impact on the swelling and population control ability of the insecticidal delivery composition (e.g., swelling and controllability of the superabsorbent polymer alone and/or the release rate of certain insecticidal agents that may be impregnated there within). Therefore, it is possible to utilize certain salts in superabsorbent polymer-base formulations as another mechanism to alter (enhance in this case) or adjust the release rate of these formulations. The salt content of the aquatic habitat may also have an effect on kill of the target species by affecting the matrix swelling, breakdown, decomposition, and/or release of active insecticidal ingredients. The addition of salts to the matrix formulation may also affect a mechanism to vary this factor.

The following are examples of comparative bioassays that demonstrate effective control of larvae, pupae, and/or emerging adults of a variety of mosquito species with single and joint action formulations of a superabsorbent polymer and one or more insect control agents. All parts, percentages and ratios are by weight unless otherwise noted.

EXAMPLES I–VII

Data was collected from the use of an insecticidal delivery compound made up of starch, acrylonitrile copolymer (Super Sorb) as the superabsorbent polymer and film-forming agent isostearyl alcohol containing two oxyethylene groups (Arosurf® MSF), and Super Sorb, Arosurf® MSF and *B.t.i.*, or *B. sphaericus*, or Abate® 4-E. Arosurf® MSF is the only film-forming agent (so-called monomolecular surface film) that is presently registered by the Environmental Protection Agency (E.P.A.) for use as a mosquito larvicide and pupicide and licensed under U.S. Pat. No. 4,160, 033. *B.t.i.* products and Abate® 4-E have E.P.A. registration while *B. sphaericus* (BSP-1) has an E.P.A. experimental use permit pending E.P.A. registration. Other bioassays were conducted with the starch graft polymer 2-propenamide-co-2-propenoic acid, sodium salt (Water Lock® Superabsorbent Polymer G-100) as the superabsorbent polymer and Arosurf® MSF, and Water Lock® G-100, Arosurf® MSF and *B.t.i.*, or *B. sphaericus*, or Abate® 4-E. Although similar results were obtained, the bioassays indicated that the overall mosquito-controlling efficacy was better with Super Sorb. Also, 50/50 blends of Super Sorb and Water Lock® Superabsorbent Polymer G-100 were evaluated in combination with the aforementioned active insecticidal ingredients with comparable mosquito-controlling efficacy being observed.

Film-forming agents such as sorbitan monooleate, oleyl alcohol, 75% sorbitan monooleate and 25% 2-ethyl butanol or 2- propanol, olyel alcohol containing 2 oxyethylene groups, and lauryl ether containing 4 oxyethylene groups were also evaluated. These materials were impregnated onto Super Sorb and Water Lock® G-100 to determine mixing compatibility and surface film release only. Although these materials were not evaluated against larvae and pupae, results of film-release studies suggested that comparable mosquito-controlling efficacy would result. In addition, the insect growth regulator Altosid® SR-10 was also formulated with Arosurf® MSF and Super Sorb or Water Lock® G-100, to determine formulation compatibilities. Results indicate that joint action formulations of these materials can also be utilized.

In general, the data indicates that liquid film-forming or surface active agents can be mixed with, and impregnated on, a superabsorbent polymer matrix, alone, or in combination with one or more liquid or solid mosquito larvicides, ovicides, pupicides, insecticides, pesticides, biological control agents, microbial control agents, pathogens, parasites, conventional toxicants, and insect growth regulators, to produce single, joint or multiple action solid formulations for single and multi-stage mosquito control in the aquatic environment.

Surprisingly, the data indicates that formulations of Super Sorb and Arosurf® MSF produced faster control of larvae of *Aedes taeniorhynchus* than Arosurf® MSF alone. The data suggests that the two-component formulation may produce an activation or larvicidal enhancement mechanism for Arosurf® MSF against this mosquito species in the water qualities tested. It should be noted that the superabsorbent polymer alone showed no significant larvicidal activity.

In general, polymer-base larvicidal enhancement was not observed in tests against *Culex quinquefasciatus* and *Aedes aegypti*. Tests against these species in fresh water showed comparable larvicidal efficacy when the superabsorbent polymer-Arosurf® MSF formulation was evaluated against Arosurf® MSF alone. It should be noted that larvae of the *Ae. taeniorhynchus* are significantly more sensitive to Arosurf ® MSF than *Cx. quinquefasciatus* or *Ae aegypti*. However, it should be noted that the salt marsh mosquito *Aedes taeniorhynchus* is the main pest mosquito in Lee County as well as in other coastal counties of Florida and other parts of the U.S.A.

TABLE I

Efficacy of superabsorbent polymer-base formulations of Arosurf ® MSF against larvae of *Aedes taeniorhynchus*.[1]

| Run no. | Larval instar | Formulation | Application rate per surface acre | Cumulative percentage mortality of larvae, pupae, and/or emerging adults at indicated posttreatment time period (days)[4] | | | | | |
|---|---|---|---|---|---|---|---|---|---|
| | | | | 1 | 2 | 3 | 4 | 5 | 6 |
| 1 | 1st | Polymers + Arosurf MSF | 4.4 lb[2] | 0 | 36.7 | 76.7 | 96.7 | — | — |
| | | Arosurf MSF | 0.26 gal | 0 | 0 | 10 | 40 | — | — |
| | | Polymers | 2.2 lb | 6.7 | 6.7 | 6.7 | 6.7 | — | — |
| | | Control | — | 0 | 6.7 | 6.7 | 6.7 | — | — |
| 2 | 2nd | Polymers + Arosurf MSF | 4.4 lb | 16.7 | 80 | 96.7 | 96.7 | 100 | — |
| | | Arosurf MSF | 0.26 gal | 0 | 6.7 | 83.3 | 93.3 | 100 | — |
| | | Polymers | 2.2 lb | 3.3 | 3.3 | 3.3 | 3.3 | 3.3 | — |
| | | Control | — | 0 | 0 | 6.7 | 13.3 | 13.3 | — |
| 3 | 3rd | Polymers + Arosurf MSF | 4.4 lb | 6.7 | 100 | — | — | — | — |
| | | Arosurf MSF | 0.26 gal. | 3.3 | 80 | 83.3 | 86.7 | — | — |
| | | Polymers | 2.2 lb | 0 | 0 | 0 | 3.3 | — | — |
| | | Control | — | 0 | 0 | 0 | 0 | — | — |
| 4 | 3rd | Polymers + Arosurf MS | 4.4 lb | 6.7 | 56.7 | 76.7 | 83.3 | 90 | — |
| | | Arosurf MSF | 0.26 gal | 16.7 | 36.7 | 53.3 | 56.7 | 56.7 | — |
| | | Polymers | 2.2 lb | 0 | 0 | 0 | 13.3 | 13.3 | — |
| | | Control | — | 0 | 0 | 3.3 | 3.3 | 10 | — |
| 5 | 3rd | Polymers + Arosurf MSF | 4.4 lb | 53.3 | 93.3 | 93.3 | 96.7 | 100 | — |
| | | Arosurf MSF | 0.26 gal | 10 | 93.3 | 96.7 | 96.7 | 96.7 | 100 |
| | | Polymers | 2.2 lb | 0 | 0 | 0 | 0 | 0 | 0 |
| | | Control | — | 0 | 0 | 3.3 | 3.3 | 3.3 | 3.3 |
| 6 | 3rd | Polymers + Arosurf MSF | 4.4 lb | 26.7 | 100 | — | — | — | — |
| | | Arosurf MSF | 0.26 gal | 43.3 | 100 | — | — | — | — |
| | | Polymers | 2.2 lb | 0 | 0 | — | — | — | — |
| | | Control | — | 0 | 0 | — | — | — | — |
| 7 | 3rd | Polymers + Arosurf MSF | 4.4 lb | 100 | — | — | — | — | — |
| | | Arosurf MSF | 0.26 gal | 80 | 100 | — | — | — | — |
| | | Polymers | 2.2 lb | 3.3 | 3.3 | — | — | — | — |
| | | Control | — | 0 | 0 | — | — | — | — |
| 8 | 3rd | Polymers + Arosurf MSF | 4.4 lb | 23.3 | 53.3 | 100 | — | — | — |
| | | Arosurf MSF | 0.26 gal | 53.3 | 63.3 | 100 | — | — | — |
| | | Polymers | 2.2 lb | 0 | 0 | 0 | — | — | — |
| | | Control | — | 0 | 3.3 | 3.3 | — | — | — |
| 9 | 3rd | Polymers + Arosurf MSF | 6.6 lb[3] | 26.7 | 90 | 100 | — | — | — |
| | | Arosurf MSF | 0.26 gal | 3.3 | 63.3 | 100 | — | — | — |
| | | Arosurf MSF | 0.52 gal | 0 | 46.7 | 100 | — | — | — |
| | | Polymers | 6.6 lb | 0 | 0 | 0 | — | — | — |
| | | Control | — | 0 | 3.3 | 3.3 | — | — | — |
| 10 | 3rd | Polymers + Arosurf MSF | 6.6 lb | 13.3 | 56.7 | 100 | — | — | — |
| | | Arosurf MSF | 0.26 gal | 0 | 50 | 93.3 | 93.3 | 93.3 | 100 |
| | | Arosurf MSF | 0.52 gal | 0 | 43.3 | 93.3 | 100 | — | — |
| | | Polymers | 6.6 lb | 0 | 0 | 3.3 | 6.7 | 6.7 | 6.7 |
| | | Control | — | 3.3 | 3.3 | 3.3 | 3.3 | 6.7 | 6.7 |
| 11 | 3rd | Polymers + Arosurf MSF | 6.6 lb | 60 | 83.3 | 90 | 90 | 100 | — |
| | | Arosurf MSF | 0.26 gal | 46.7 | 63.3 | 76.7 | 90 | 93.3 | 100 |
| | | Polymers | 3.3 lb | 0 | 0 | 3.3 | 3.3 | 3.3 | 6.7 |
| | | Control | — | 0 | 0 | 6.7 | 6.7 | 10 | 10 |
| 12 | 4th | Polymers + Arosurf MSF | 4.4 lb | 0 | 60 | 96.7 | — | — | — |
| | | Arosurf MSF | 0.26 gal | 0 | 33.3 | 56.7 | — | — | — |
| | | Polymers | 2.2 lb | 0 | 0 | 0 | — | — | — |
| | | Control | — | 0 | 0 | 0 | — | — | — |
| 13 | 4th | Polymers + Arosurf MSF | 4.4 lb | 3.3 | 20 | 43.3 | 76.7 | 90 | — |
| | | Arosurf MSF | 0.26 gal | 6.7 | 10 | 26.7 | 53.3 | 63.3 | — |
| | | Polymers | 2.2 lb | 6.7 | 6.7 | 10 | 13.3 | 13.3 | — |
| | | Control | — | 0 | 0 | 3.3 | 3.3 | 13.3 | — |
| 14 | 4th | Polymers + Arosurf MSF | 6.6 lb | 86.7 | 100 | — | — | — | — |
| | | Arosurf MSF | 0.26 gal | 40 | 66.7 | 80 | 83.3 | 96.7 | 100 |
| | | Arosurf MSF | 0.52 gal | 36.7 | 70 | 83.3 | 86.7 | 96.7 | 100 |
| | | Polymers | 3.3 lb | 0 | 0 | 3.3 | 3.3 | 6.7 | 6.7 |
| | | Control | — | 0 | 0 | 6 | 0 | 3.3 | 3.3 |

TABLE I-continued

Efficacy of superabsorbent polymer-base formulations of Arosurf ® MSF against larvae of *Aedes taeniorhynchus.*[1]

| Run no. | Larval instar | Formulation | Application rate per surface acre | Cumulative percentage mortality of larvae, pupae, and/or emerging adults at indicated posttreatment time period (days)[4] 1 | 2 | 3 | 4 | 5 | 6 |
|---|---|---|---|---|---|---|---|---|---|

[1]Starch, acrylonitrile copolymer (Super Sorb) used in all tests. Arosurf MSF lot no. 4158k used in all tests. All bioassys conducted in 12.5% artificial seawater.
[2]1:1 ratio of Polymers to Arosurf MSF with Arosurf MSF application rate of 0.23 gal/acre.
[3]1:1 ratio of Polymers to Arosurf MSF with Arosurf MSF application rate of 0.35 gal/acre.
[4]Tests terminated at highest mortality shown.

TABLE II

Effect of habitat water quality on efficacy of superabsorbent polymer-base formulations of Arosurf ® MSF against larvae of *Aedes taeniorhynchus.*[1]

| Run no. | Larval instar | % seawater[2] | Formulation (age) | Application rate per surface acre | Cumulative percentage mortality of larvae, pupae, and/or emerging adults at indicated posttreatment time period (days)[4] 1 | 2 | 3 | 4 | 5 | 6 | 7 |
|---|---|---|---|---|---|---|---|---|---|---|---|
| 1a | 2nd | 0 | Polymers + Arosurf MSF (134 days) | 4.4 lb[3] | 40 | 86.7 | 96.7 | 96.7 | 100 | — | — |
| | | | Polymers + Arosurf MSF (6 days) | 4.4 lb | 23.3 | 30 | 86.7 | 90 | 96.7 | 100 | — |
| | | | Arosurf MSF | 0.26 gal | 16.7 | 36.7 | 53.3 | 70 | 83.3 | 86.7 | 100 |
| | | | Polymers | 2.2 lb | 0 | 3.3 | 10 | 10 | 10 | 10 | 10 |
| | | | Control | — | 0 | 0 | 3.3 | 3.3 | 3.3 | 3.3 | 3.3 |
| 1b | 2nd | 6.25 | Polymers + Arosurf MSF (134 days) | 4.4 lb | 100 | — | — | — | — | — | — |
| | | | Polymers + Arosurf MSF (6 days) | 4.4 lb | 100 | — | — | — | — | — | — |
| | | | Arosurf MSF | 0.26 gal | 86.7 | 100 | — | — | — | — | — |
| | | | Polymers | 2.2 lb | 0 | 0 | — | — | — | — | — |
| | | | Control | — | 0 | 0 | — | — | — | — | — |
| 1c | 2nd | 12.5 | Polymers + Arosurf MSF (134 days) | 4.4 lb | 100 | — | — | — | — | — | — |
| | | | Polymers + Arosurf MSF (6 days) | 4.4 lb | 100 | — | — | — | — | — | — |
| | | | Arosurf MSF | 0.26 gal | 100 | — | — | — | — | — | — |
| | | | Polymers | 2.2 lb | 0 | — | — | — | — | — | — |
| | | | Control | — | 0 | — | — | — | — | — | — |
| 1d | 2nd | 25 | Polymers + Arosurf MSF (134 days) | 4.4 lb | 100 | — | — | — | — | — | — |
| | | | Polymers + Arosurf MSF (6 days) | 4.4 lb | 100 | — | — | — | — | — | — |
| | | | Arosurf MSF | 0.26 gal | 100 | — | — | — | — | — | — |
| | | | Polymers | 2.2 lb | 6.7 | — | — | — | — | — | — |
| | | | Control | — | 0 | — | — | — | — | — | — |
| 1e | 2nd | 50 | Polymers + Arosurf MSF (134 days) | 4.4 lb | 100 | — | — | — | — | — | — |
| | | | Polymers + Arosurf MSF (6 days) | 4.4 lb | 100 | — | — | — | — | — | — |
| | | | Arosurf MSF | 0.26 gal | 100 | — | — | — | — | — | — |
| | | | Polymers | 2.2 lb | 0 | — | — | — | — | — | — |
| | | | Control | — | 0 | — | — | — | — | — | — |
| 1f | 2nd | 75 | Polymers + Arosurf MSF (134 days) | 4.4 lb | 100 | — | — | — | — | — | — |
| | | | Polymers + Arosurf MSF (6 days) | 4.4 lb | 100 | — | — | — | — | — | — |
| | | | Arosurf MSF | 0.26 gal | 100 | — | — | — | — | — | — |
| | | | Polymers | 2.2 lb | 0 | — | — | — | — | — | — |
| | | | Control | — | 0 | — | — | — | — | — | — |
| 2a | 3rd | 0 | Polymers + Arosurf MSF (94 days) | 4.4 lb | 50 | 60 | 70 | 76.7 | 90 | 100 | — |
| | | | Arosurf MSF | 0.26 gal | 23.3 | 43.3 | 70 | 83.3 | 100 | — | — |
| | | | Polymers | 2.2 lb | 0 | 0 | 3.3 | 3.3 | 3.3 | — | — |
| | | | Control | — | 0 | 0 | 0 | 3.3 | 3.3 | 3.3 | — |
| 2b | 3rd | 50 | Polymers + Arosurf MSF (94 days) | 4.4 lb | 86.7 | 93.3 | 96.7 | 100 | — | — | — |
| | | | Arosurf MSF | 0.26 gal | 16.7 | 40 | 86.7 | 100 | — | — | — |

TABLE II-continued

Effect of habitat water quality on efficacy of superabsorbent polymer-base formulations of Arosurf ® MSF against larvae of *Aedes taeniorhynchus*.[1]

| Run no. | Larval instar | % seawater[2] | Formulation (age) | Application rate per surface acre | Cumulative percentage mortality of larvae, pupae, and/or emerging adults at indicated posttreatment time period (days)[4] | | | | | | |
|---|---|---|---|---|---|---|---|---|---|---|---|
| | | | | | 1 | 2 | 3 | 4 | 5 | 6 | 7 |
| | | | Polymers | 2.2 lb | 0 | 0 | 3.3 | 3.3 | — | — | — |
| | | | Control | — | 0 | 0 | 0 | 0 | — | — | — |
| 2c | 3rd | 100 | Polymers + Arosurf MSF (94 days) | 4.4 lb | 93.3 | 100 | — | — | — | — | — |
| | | | Arosurf MSF | 0.26 gal | 53.3 | 76.7 | 80 | 83.3 | 96.7 | 100 | — |
| | | | Polymers | 2.2 lb | 0 | 0 | 3.3 | 3.3 | 3.3 | 3.3 | — |
| | | | Control | — | 0 | 0 | 0 | 0 | 0 | 0 | — |
| 3a | 3rd | 0 | Polymers + Arosurf MSF (101 days) | 4.4 lb | 83.3 | 93.3 | 96.7 | 96.7 | 100 | — | — |
| | | | Polymers + Arosurf MSF (1 day) | 4.4 lb | 76.7 | 80 | 86.7 | 86.7 | 90 | 100 | — |
| | | | Arosurf MSF | 0.26 gal | 20 | 40 | 83.3 | 86.7 | 96.7 | 100 | — |
| | | | Polymers | 2.2 lb | 0 | 3.3 | 3.3 | 6.7 | 6.7 | 6.7 | — |
| | | | Control | — | 0 | 0 | 0 | 0 | 0 | 0 | — |
| 3b | 3rd | 6.25 | Polymers + Arosurf MSF (101 days) | 4.4 lb | 93.3 | 93.3 | 96.7 | 96.7 | 100 | — | — |
| | | | Polymers + Arosurf MSF (1 day) | 4.4 lb | 90 | 93.3 | 93.3 | 93.3 | 96.7 | 100 | — |
| | | | Arosurf MSF | 0.26 gal | 46.7 | 56.7 | 86.7 | 86.7 | 100 | — | — |
| | | | Polymers | 2.2 lb | 0 | 0 | 6.7 | 6.7 | 6.7 | 6.7 | — |
| | | | Control | — | 0 | 0 | 0 | 0 | 3.3 | 3.3 | — |
| 3c | 3rd | 12.5 | Polymers + Arosurf MSF (101 days) | 4.4 lb | 66.7 | 90 | 100 | — | — | — | — |
| | | | Polymers + Arosurf MSF (1 day) | 4.4 lb | 63.3 | 90 | 96.7 | 96.7 | 96.7 | 100 | — |
| | | | Arosurf MSF | 0.26 gal | 40 | 60 | 83.3 | 90 | 93.3 | 100 | — |
| | | | Polymers | 2.2 lb | 0 | 0 | 0 | 3.3 | 3.3 | 3.3 | — |
| | | | Control | — | 0 | 0 | 0 | 3.3 | 3.3 | 3.3 | — |
| 3d | 3rd | 25 | Polymers + Arosurf MSF (101 days) | 4.4 lb | 73.3 | 93.3 | 100 | — | — | — | — |
| | | | Polymers + Arosurf MSF (1 day) | 4.4 lb | 73.3 | 100 | — | — | — | — | — |
| | | | Arosurf MSF | 0.26 gal | 26.7 | 60 | 93.3 | 93.3 | 93.3 | 100 | — |
| | | | Polymers | 2.2 lb | 0 | 0 | 0 | 0 | 0 | 3.3 | — |
| | | | Control | — | 0 | 0 | 0 | 0 | 3.3 | 3.3 | — |
| 3e | 3rd | 50 | Polymers + Arosurf MSF (101 days) | 4.4 lb | 96.7 | 100 | — | — | — | — | — |
| | | | Polymers + Arosurf MSF (1 day) | 4.4 lb | 93.3 | 100 | — | — | — | — | — |
| | | | Arosurf MSF | 0.26 gal | 46.7 | 80 | 100 | — | — | — | — |
| | | | Polymers | 2.2 lb | 0 | 0 | 3.3 | — | — | — | — |
| | | | Control | — | 0 | 0 | 0 | — | — | — | — |
| 3f | 3rd | 100 | Polymers + Arosurf MSF (101 days) | 4.4 lb | 83.3 | 96.7 | 100 | — | — | — | — |
| | | | Polymers + Arosurf MSF (1 day) | 4.4 lb | 83.3 | 96.7 | 100 | — | — | — | — |
| | | | Arosurf MSF | 0.26 gal | 40 | 46.7 | 83.3 | 96.7 | 100 | — | — |
| | | | Polymers | 2.2 lb | 0 | 0 | 0 | 0 | 0 | — | — |
| | | | Control | — | 0 | 0 | 0 | 0 | 3.3 | — | — |
| 4a | 4th | 6.25 | Polymers + Arosurf MSF (136 days) | 4.4 lb | 100 | — | — | — | — | — | — |
| | | | Polymers + Arosurf MSF (8 days) | 4.4 lb | 93.3 | 100 | — | — | — | — | — |
| | | | Arosurf MSF | 0.26 gal | 90 | 93.3 | 100 | — | — | — | — |
| | | | Polymers | 2.2 lb | 3.3 | 3.3 | 3.3 | — | — | — | — |
| | | | Control | — | 6.7 | 6.7 | 6.7 | — | — | — | — |
| 4b | 4th | 12.5 | Polymers + Arosurf MSF (136 days) | 4.4 lb | 100 | — | — | — | — | — | — |
| | | | Polymers + Arosurf MSF (8 days) | 4.4 lb | 96.7 | 100 | — | — | — | — | — |
| | | | Arosurf MSF | 0.26 gal | 53.3 | 80 | 90 | 100 | — | — | — |
| | | | Polymers | 2.2 lb | 3.3 | 3.3 | 3.3 | 3.3 | — | — | — |
| | | | Control | — | 0 | 0 | 0 | 0 | — | — | — |
| 4c | 4th | 25 | Polymers + Arosurf MSF (136 days) | 4.4 lb | 100 | — | — | — | — | — | — |
| | | | Polymers + Arosurf MSF (8 days) | 4.4 lb | 100 | — | — | — | — | — | — |
| | | | Arosurf MSF | 0.26 gal | 56.7 | 63.3 | 70 | 100 | — | — | — |
| | | | Polymers | 2.2 lb | 0 | 3.3 | 3.3 | 3.3 | — | — | — |
| | | | Control | — | 3.3 | 3.3 | 3.3 | 3.3 | — | — | — |

TABLE II-continued

Effect of habitat water quality on efficacy of superabsorbent polymer-base formulations of Arosurf ® MSF against larvae of *Aedes taeniorhynchus*.[1]

| Run no. | Larval instar | % seawater[2] | Formulation (age) | Application rate per surface acre | Cumulative percentage mortality of larvae, pupae, and/or emerging adults at indicated posttreatment time period (days)[4] | | | | | | |
|---|---|---|---|---|---|---|---|---|---|---|---|
| | | | | | 1 | 2 | 3 | 4 | 5 | 6 | 7 |
| 4d | 4th | 50 | Polymers + Arosurf MSF (136 days) | 4.4 lb | 100 | — | — | — | — | — | — |
| | | | Polymers + Arosurf MSF (8 days) | 4.4 lb | 100 | — | — | — | — | — | — |
| | | | Arosurf MSF | 0.26 gal | 33.3 | 56.7 | 83.3 | 100 | — | — | — |
| | | | Polymers | 2.2 lb | 0 | 3.3 | 3.3 | 3.3 | — | — | — |
| | | | Control | — | 0 | 0 | 0 | 0 | — | — | — |
| 4e | 4th | 75 | Polymers + Arosurf MSF (136 days) | 4.4 lb | 100 | — | — | — | — | — | — |
| | | | Polymers + Arosurf MSF (8 days) | 4.4 lb | 96.7 | 100 | — | — | — | — | — |
| | | | Arosurf MSF | 0.26 gal | 60 | 83.3 | 93.3 | 100 | — | — | — |
| | | | Polymers | 2.2 lb | 0 | 0 | 0 | 0 | — | — | — |
| | | | Control | 2.2 lb | 0 | 0 | 0 | 0 | — | — | — |
| 5a | 4th | 0 | Polymers + Arosurf MSF (60 days) | 4.4 lb | 83.3 | 100 | — | — | — | — | — |
| | | | Arosurf MSF | 0.26 gal | 43.3 | 96.7 | 100 | — | — | — | — |
| | | | Polymers | 2.2 lb | 0 | 3.3 | 3.3 | — | — | — | — |
| | | | Control | — | 0 | 0 | 6.7 | — | — | — | — |
| 5b | 4th | 100 | Polymers + Arosurf MSF (60 days) | 4.4 lb | 96.7 | 96.7 | 100 | — | — | — | — |
| | | | Arosurf MSF | 0.26 gal | 40 | 63.3 | 96.7 | 100 | — | — | — |
| | | | Polymers | 2.2 lb | 0 | 3.3 | 6.7 | 6.7 | — | — | — |
| | | | Control | — | 0 | 0 | 6.7 | 6.7 | — | — | — |

[1] Starch, acrylonitrile copolymer (Super Sorb) used in all tests. Arosurf MSF lot no. 4158k used in all tests.
[2] Seawater concentrations of 0–100% prepared with Instant Ocean and water purified by reverse osmosis (RO); 0% seawater = RO water.
[3] 1:1 ratio of Polymers to Arosurf MSF with Arosurf MSF application rate of 0.23 gal/acre.
[4] Tests terminated at highest mortality shown.

The data also indicates that these powdered superabsorbent polymers can be agglomerated with various concentrations of Arosurf® MSF or other film-forming chemicals by conventional techniques to produce granules that possess larvicidal and pupicidal efficacy that is comparable to the non-agglomerated superabsorbent polymer formulations. Both quick and slow-release formulations may be made in granule form.

TABLE III

Comparative efficacy of agglomerated and non-agglomerated superabsorbent polymer-base formulations of Arosurf ® MSF against larvae and pupae (P) of *Aedes taeniorhynchus* (A.T.) and *Culex quinquefasciatus* (C.Q.).[1]

| Run (No.) | Species (instar/ pupae) | Water quality (% sea-water) | Formulation | Application rate per surface acre[2] | Cumulative percentage mortality of larvae, pupae, and/or emerging adults at indicated posttreatment time period (days) | | | | | | |
|---|---|---|---|---|---|---|---|---|---|---|---|
| | | | | | 1 | 2 | 3 | 4 | 5 | 6 | 7 |
| 1a | A.T. (4th) | 6.25 | Polymers + Arosurf MSF (Agglomerated) | 3.52 lb | 60 | 80 | 86.7 | 90 | 93.3 | 100 | — |
| | | | Polymers + Arosurf MSF (Non-agglomerated) | 4.4 lb | 66.7 | 93.3 | 96.7 | 96.7 | 96.7 | 96.7 | 100 |
| | | | Control | — | 0 | 0 | 0 | 3.3 | 3.3 | 3.3 | 3.3 |
| 1b | A.T. (4th) | 12.5 | Polymers + Arosurf MSF (Agglomerated) | 3.52 lb | 76.7 | 93.3 | 96.7 | 100 | — | — | — |
| | | | Polymers + Arosurf MSF (Non-agglomerated) | 4.4 lb | 90 | 100 | — | — | — | — | — |
| | | | Control | — | 0 | 3.3 | 3.3 | 3.3 | — | — | — |
| 1c | A.T. (4th) | 25 | Polymers + Arosurf MSF (Agglomerated) | 3.52 lb | 83.3 | 96.7 | 100 | — | — | — | — |
| | | | Polymers + Arosurf MSF (Non-agglomerated) | 4.4 lb | 80 | 96.7 | 100 | — | — | — | — |
| | | | Control | — | 3.3 | 3.3 | 3.3 | — | — | — | — |
| 2 | C.Q. (4th/P) | R.O.[3] | Polymers + Arosurf MSF (Agglomerated) | 4.4 lb | 6.7 | 53.3 | 86.7 | 96.7[4] | — | — | — |
| | | | Polymers + Arosurf MSF (Agglomerated) | 6.6 lb | 13.3 | 66.7 | 90 | 100 | — | — | — |

TABLE III-continued

Comparative efficacy of agglomerated and non-agglomerated superabsorbent polymer-base formulations of Arosurf ® MSF against larvae and pupae (P) of *Aedes taeniorhynchus* (A.T.) and *Culex quinquefasciatus* (C.Q.).[1]

| Run (No.) | Species (instar/ pupae) | Water quality (% sea- water) | Formulation | Application rate per surface acre[2] | Cumulative percentage mortality of larvae, pupae, and/or emerging adults at indicated posttreatment time period (days) | | | | | | |
|---|---|---|---|---|---|---|---|---|---|---|---|
| | | | | | 1 | 2 | 3 | 4 | 5 | 6 | 7 |
| | | | Polymers + Arosurf MSF (Non-agglomerated) | 4.4 lb | 6.7 | 53.3 | 86.7 | 93.3[5] | — | — | — |
| | | | Polymers + Arosurf MSF (Non-agglomerated) | 6.6 lb | 26.7 | 66.7 | 96.7 | 100 | — | — | — |
| | | | Arosurf MSF | 0.26 gal | 10 | 63.3 | 86.7 | 100 | — | — | — |
| | | | Control | — | 0 | 0 | 3.3 | 3.3 | — | — | — |
| 3 | C.Q. (4th) | R.O. | Polymers + Arosurf MSF (Agglomerated) | 4.4 lb | 10 | 10 | 26.7 | 70 | 100 | — | — |
| | | | Polymers + Arosurf MSF (Agglomerated) | 6.6 lb | 6.7 | 16.7 | 43.3 | 80 | 100 | — | — |
| | | | Polymers + Arosurf MSF (Non-agglomerated) | 4.4 lb | 3.3 | 10 | 63.3 | 83.3 | 96.7[4] | — | — |
| | | | Polymers + Arosurf MSF (Non-agglomerated) | 6.6 lb | 13.3 | 36.7 | 46.7 | 76.7 | 100 | — | — |
| | | | Arosurf MSF | 0.26 gal | 20 | 37.7 | 43.3 | 85.7 | 100 | — | — |
| | | | Control | — | 0 | 0 | 0 | 3.3 | 3.3 | — | — |

[1]Starch, acrylonitrile copolymer (Super Sorb) used in all tests. Arosurf MSF lot no. 4158k used in all tests. 1/16 inch diameter agglomerated granules produced using a Turbulator/Disc Pelletizer combination (Femo-Tech, Wyandotte, Michigan).
[2]Application rates of 3.52, 4.4, and 6.6 lb/acre of agglomerated Polymers + Arosurf MSF resulted in active ingredient being applied at ca. 0.23, 0.29, and 0.44 gal/acre Arosurf MSF, respectively. Application rates of 4.4 and 6.6 lb/acre of non-agglomerated Polymers + Arosurf MSF resulted in active ingredient being applied at ca. 0.23 and 0.35 gal/acre Arosurf MSF, respectively.
[3]0% seawater = R.O. water.
[4]3.3% adult escapees.
[5]6.7% adult escapees.

Surprisingly, additional data indicates that mixtures of Super Sorb (and Water Lock® G-100 ) and Arosurf® MSF and *Bacillus thuringiensis* var. *israelensis* or *Bacillus sphaericus* or Abate® 4-E produce joint action solid formulations that would kill larvae, pupae and emerging adults significantly better than any of the formulation components.

The superabsorbent polymer formulation techniques disclosed, are expected to improve ground and aerial application and vegetative penetration procedures for a variety of insecticidal formulations. It is expected that these superabsorbent polymer matrices will form the basis for a series of floating and submerged quick and controlled release products that are self-spreading when introduced into water.

TABLE IV

Efficacy of superabsorbent polymer-base formulations of Arosurf ® MSF and *Bacillus sphaericus* against immature stages of *Culex quinquefasciatus*.[1]

| Run no. | Larval instar/ pupae (P) | Formulation (age) | Application rate per surface acre | Cumulative percentage mortality of larvae, pupae, and/or emerging adults at indicated posttreatment time period (days)[10] | | | | | | | % adult emergence |
|---|---|---|---|---|---|---|---|---|---|---|---|
| | | | | 1 | 2 | 3 | 4 | 5 | 6 | 7 | |
| 1 | 4th/P | Polymers + Arosurf MSF + *B. sphaericus* (39 days) | 4.4 lb[2] | 50 | 100 | — | — | — | — | — | 0 |
| | | *B. sphaericus* + water (1 day) | 5.0 gal[3] | 50 | 50 | — | — | — | — | — | 50 |
| | | Arosurf MSF + water (1 day) | 5.0 gal[4] | 6.7 | 56.7 | 86.7 | 100 | — | — | — | 0 |
| | | Arosurf MSF | 0.26 gal[4] | 10 | 63 | 86.7 | 100 | — | — | — | 0 |
| | | Polymers + Arosurf MSF (6 days) | 4.4 lb[5] | 6.7 | 53.3 | 86.7 | 96.7 | — | — | — | 3.3 |
| | | Polymers + Arosurf MSF (6 days) | 6.6 lb[6] | 26.7 | 66.7 | 96.7 | 100 | — | — | — | 0 |
| | | Control | — | 0 | 0 | 0 | 3.3 | — | — | — | 96.7 |
| 2 | 4th/P | Polymers + Arosurf MSF + *B. sphaericus* (21 days) | 4.4 lb | 30 | 100 | — | — | — | — | — | 0 |
| | | *B. sphaericus* + Arosurf MSF (21 days) | 0.26 gal[7] | 40 | 100 | — | — | — | — | — | 0 |
| | | *B. sphaericus* + water (1 day) | 5.0 gal | 23.3 | 30 | 33.3 | — | — | — | — | 66.7 |
| | | Arosurf MSF + water (1 day) | 5.0 gal | 43.3 | 96.7 | 100 | — | — | — | — | 0 |
| | | Arosurf MSF | 0.26 gal | 46.7 | 90 | 100 | — | — | — | — | 0 |

TABLE IV-continued

Efficacy of superabsorbent polymer-base formulations of Arosurf ® MSF and *Bacillus sphaericus* against immature stages of *Culex quinquefasciatus*.[1]

| Run no. | Larval instar/ pupae (P) | Formulation (age) | Application rate per surface acre | Cumulative percentage mortality of larvae, pupae, and/or emerging adults at indicated posttreatment time period (days)[10] | | | | | | | % adult emergence |
|---|---|---|---|---|---|---|---|---|---|---|---|
| | | | | 1 | 2 | 3 | 4 | 5 | 6 | 7 | |
| | | Polymers + Arosurf MSF (96 days) | 4.4 lb | 43.3 | 86.7 | 100 | — | — | — | — | 0 |
| | | Polymers | 2.2 lb[8] | 0 | 3.3 | 3.3 | — | — | — | — | 96.7 |
| | | Control | — | 3.3 | 3.3 | 3.3 | — | — | — | — | 96.7 |
| 3 | 4th | Polymers + Arosurf MSF + B. sphaericus (1 day) | 4.4 lb | 90 | 100 | — | — | — | — | — | 0 |
| | | Polymers + Arosurf MSF + B. sphaericus (38 days) | 4.4 lb | 96.7 | 100 | — | — | — | — | — | 0 |
| | | B. sphaericus + water (1 day) | 5.0 gal | 100 | — | — | — | — | — | — | 0 |
| | | Arosurf MSF | 0.26 gal | 20 | 36.7 | 43.3 | 86.7 | 100 | — | — | 0 |
| | | Polymers + Arosurf MSF (5 days) | 4.4 lb | 3.3 | 10 | 30 | 63.3 | 83.3 | — | — | 16.7 |
| | | Polymers + Arosurf MSF (5 days) | 6.6 lb | 13.3 | 36.7 | 46.7 | 76.7 | 100 | — | — | 0 |
| | | Control | — | 0 | 0 | 0 | 3.3 | 3.3 | — | — | 96.7 |
| 4 | 4th | Polymers + Arosurf MSF + B. sphaericus (1 day) | 4.4 lb[9] | 100 | — | — | — | — | — | — | 0 |
| | | B. sphaericus + water (1 day) | 5.0 gal | 100 | — | — | — | — | — | — | 0 |
| | | B. sphaericus + Arosurf MSF (1 day) | 0.26 gal | 100 | — | — | — | — | — | — | 0 |
| | | Arosurf MSF | 0.26 gal | 0 | 6.7 | 66.7 | 100 | — | — | — | 0 |
| | | Polymers + Arosurf MSF (1 day) | 4.4 lb | 0 | 6.7 | 66.7 | 100 | — | — | — | 0 |
| | | Polymers | 2.2 lb | 10 | 10 | 10 | 10 | — | — | — | 90 |
| | | Control | — | 0 | 0 | 3.3 | 3.3 | — | — | — | 96.7 |
| 5 | 3rd | Polymers + Arosurf MSF + B. sphaericus (35 days) | 4.4 lb | 96.7 | 100 | — | — | — | — | — | 0 |
| | | B. sphaericus + Arosurf MSF (35 days) | 0.26 gal | 96.7 | 100 | — | — | — | — | — | 0 |
| | | B. sphaericus + water (1 day) | 5.0 gal | 100 | — | — | — | — | — | — | 0 |
| | | Arosurf MSF + water (1 day) | 5.0 gal | 3.3 | 6.7 | 26.7 | 70 | 100 | — | — | 0 |
| | | Arosurf MSF | 0.26 gal | 10 | 16.7 | 23.3 | 50 | 100 | — | — | 0 |
| | | Polymers + Arosurf MSF (105 days) | 4.4 lb | 6.7 | 6.7 | 10 | 40 | 67.6 | 90 | 93.3 | 6.7 |
| | | Polymers + Arosurf MSF (105 days) | 6.6 lb | 6.7 | 10 | 23.3 | 67.6 | 100 | — | — | 0 |
| | | Polymers | 2.2 lb | 0 | 0 | 0 | 3.3 | 3.3 | 3.3 | 6.7 | 93.3 |
| | | Control | — | 0 | 0 | 0 | 0 | 3.3 | 3.3 | 3.3 | 96.7 |
| 6 | 3rd | Polymers + Arosurf MSF + B. sphaericus (30 days) | 4.4 lb | 100 | — | — | — | — | — | — | 0 |
| | | B. sphaericus + Arosurf MSF (30 days) | 0.26 gal | 100 | — | — | — | — | — | — | 0 |
| | | B. sphaericus + water (1 day) | 5.0 gal | 100 | — | — | — | — | — | — | 0 |
| | | Arosurf MSF + water (1 day) | 5.0 gal | 6.7 | 13.3 | 73.3 | 100 | — | — | — | 0 |
| | | Arosurf MSF | 0.26 gal | 6.7 | 16.7 | 63.3 | 100 | — | — | — | 0 |
| | | Polymers + Arosurf MSF (100 days) | 4.4 lb | 6.7 | 10 | 63.3 | 86.7 | — | — | — | 13.3 |
| | | Polymers + Arosurf MSF (100 days) | 6.6 lb | 6.7 | 13.3 | 73.3 | 100 | — | — | — | 0 |
| | | Polymers | 2.2 lb | 0 | 0 | 0 | 0 | — | — | — | 100 |
| | | Control | — | 0 | 0 | 0 | 0 | — | — | — | 100 |

[1]Starch, acrylonitrile copolymer (Super Sorb) used in all tests. Arosurf MSF lot no. 4158k used in all tests. Flowable concentrate of *B. sphaericus* (strain 2362) used in all tests is an EUP product of Biochem Products. All tests conducted in water purified by reverse osmosis filtration (RO).
[2]Active ingredients applied at rates of 0.25 pt/acre for *B. sphaericus* and 0.12 gal/acre for Arosurf MSF.
[3]*B. sphaericus* applied at a rate of 0.25 pt/acre.
[4]Arosurf MSF applied at a rate of 0.26 gal/acre.
[5]Active ingredients applied at a rate of 0.23 gal/acre for Arosurf MSF.
[7]Active ingredients applied at a rate of 0.35 gal/acre for Arosurf MSF.
[7]Active ingredients applied at a rate of 0.25 pt/acre for *B. sphaericus* and 0.23 gal/acre for Arosurf MSF.
[8]Polymer matrix applied alone.
[9]*B. sphaericus* in test nos. 4 and 5 applied at rate of 0.5 pt/acre.
[10]50% control of mixed larvae and pupae with *B. sphaericus* alone = 100% control of larvae and 0% control of pupae.

TABLE V

Efficacy of superabsorbent polymer-base formulations of Arosurf ® MSF and Abate ® 4-E against immature stages of *Aedes taeniorhynchus* (A.T.), *Culex quinguefasciatus* (C.Q.), and *Aedes aegypti* (A.A.).[1]

| Run no. | Species | Larval instar/ pupae (P) | Formulation (Age) | Application rate per surface acre | Cumulative percentage mortality of larvae, pupae, and/or emerging adults at indicated posttreatment time period (days)[7] | | | |
|---|---|---|---|---|---|---|---|---|
| | | | | | 1 | 2 | 3 | 4 |
| 1 | A.T. | 4th | Polymers + Arosurf MSF + Abate 4-E (1 day) | 4.4 lb[2] | 100 | — | — | — |
| | | | Polymers + Arosurf MSF + Abate (28 days) | 4.4 lb | 100 | — | — | — |
| | | | Abate 4-E + water | 5.0 gal[3] | 100 | — | — | — |
| | | | Arosurf MSF | 0.26 gal[4] | 13.3 | 60 | 70 | — |
| | | | Control | — | 0 | 3.3 | 3.3 | — |
| 2 | A.T. | 4th/P | Polymers + Arosurf MSF + Abate 4-E | 4.4 lb | 100 | — | — | — |
| | | | Abate 4-E + water | 5.0 gal | 50[6] | — | — | — |
| | | | Arosurf MSF | 0.26 gal | 66.7 | 83.3 | 100 | — |
| | | | Control | — | 0 | 0 | 3.3 | — |
| 3 | C.Q. | 4th | Polymers + Arosurf MSF + Abate 4-E (1 day) | 4.4 lb | 100 | — | — | — |
| | | | Polymers + Abate 4-E (28 days) | 4.4 lb | 100 | — | — | — |
| | | | Abate 4-E + water | 5.0 gal | 100 | — | — | — |
| | | | Arosurf MSF | 0.26 gal | 13.3 | 20 | 53.3 | 66.7 |
| | | | Arosurf MSF + water | 5.0 gal[4] | 23.3 | 26.7 | 36.7 | 40 |
| | | | Control | — | 0 | 3.3 | 3.3 | 3.3 |
| 4 | A.A. | 4th | Polymers + Arosurf MSF + Abate 4-E (1 day) | 4.4 lb | 100 | — | — | — |
| | | | Polymers + Arosurf MSF + Abate 4-E (28 days) | 4.4 lb | 100 | — | — | — |
| | | | Abate 4-E + water | 5.0 gal | 100 | — | — | — |
| | | | Arosurf MSF | 0.26 gal | 0 | 0 | — | — |
| | | | Control | — | 0 | 0 | — | — |
| 5 | A.A. | 4th/P | Polymers + Arosurf MSF + Abate 4-E | 4.4 lb | 83.3 | 100 | — | — |
| | | | Abate 4-E + water | 5.0 gal | 43.3 | 43.3 | 43.3 | 43.3[5] |
| | | | Arosurf MSF | 0.26 gal | 16.7 | 30 | 43.3 | 53.3 |
| | | | Control | — | 0 | 3.3 | 3.3 | 3.3 |

[1] Starch, acrylonitrile copolymer (Super Sorb) used in all tests. Arosurf MSF lot no. 4158k used in all tests. Abate 4-E is an organophosphate larvicide of American Cyanamid Company. A.T., C.Q., A.A. tested in 12.5% seawater, sewage, and R.O. water, respectively.
[2] Active ingredients applied at 0.25 gal/acre for Arosurf MSF and 1.0 fl oz/acre for Abate 4-E.
[3] Abate 4-E applied at a rate of 1.0 fl oz/acre.
[4] Arosurf MSF applied at a rate of 0.26 gal/acre.
[5] 56.7% adult escapees.
[6] 50% adult escapees.
[7] 50% control of mixed larvae and pupae with water-base Abate 4-E alone = 100% control of larvae and 0% control of pupae. Test terminated at highest mortality shown.

TABLE VI

Efficacy of superabsorbent polymer-base formulations of Arosurf ® MSF and *Bacillus thuringiensis israelensis* (B.t.i.) against immature stages of *Aedes taeniorhynchus* (A.T.), *Culex quinquefasciatus* (C.Q.), and *Aedes aegypti* (A.A.).[1]

| Run no. | Species[2] | Larval instar/ pupae (P) | Formulation (age) | Application rate per surface acre[3,4] | Cumulative percentage mortality of larvae, pupae, and/or emerging adults at indicated posttreatment time period (days)[10] | | | | |
|---|---|---|---|---|---|---|---|---|---|
| | | | | | 1 | 2 | 3 | 4 | 5 |
| 1 | A.T. | 3rd | Polymers + Arosurf MSF + B.t.i. (1 day) | 4.4 lb | 100 | — | — | — | — |
| | | | B.t.i. + water (1 day) | 5.0 gal | 100 | — | — | — | — |
| | | | Arosurf MSF | 0.26 gal | 80 | 100 | — | — | — |
| | | | Polymers | 2.2 lb | 3.3 | 3.3 | — | — | — |
| | | | Control | — | 0 | 0 | — | — | — |
| 2 | A.T. | 4th | Polymers + Arosurf MSF + B.t.i. (1 day) | 4.4 lb | 90 | 96.7 | 100 | — | — |
| | | | Polymers + Arosurf MSF + B.t.i. (28 days) | 4.4 lb | 76.7 | 100 | — | — | — |
| | | | B.t.i. + water | 5.0 gal | 90 | 100 | — | — | — |
| | | | Arosurf MSF | 0.26 gal | 13.3 | 60 | 70 | — | — |

TABLE VI-continued

Efficacy of superabsorbent polymer-base formulations of Arosurf ® MSF and *Bacillus thuringiensis israelensis* (B.t.i.) against immature stages of *Aedes taeniorhynchus* (A.T.), *Culex quinquefasciatus* (C.Q.), and *Aedes aegypti* (A.A.).[1]

| Run no. | Species[2] | Larval instar/ pupae (P) | Formulation (age) | Application rate per surface acre[3,4] | Cumulative percentage mortality of larvae, pupae, and/or emerging adults at indicated posttreatment time period (days)[10] | | | | |
|---|---|---|---|---|---|---|---|---|---|
| | | | | | 1 | 2 | 3 | 4 | 5 |
| | | | Control | — | 0 | 3.3 | 3.3 | — | — |
| 3 | A.T. | 4th (late) | Polymers + Arosurf MSF + B.t.i. (15 days) | 4.4 lb | 96.7 | 100 | — | — | — |
| | | | B.t.i. + water (1 day) | 5.0 gal | 70 | 70[5] | — | — | — |
| | | | Arosurf MSF | 0.26 gal | 70 | 86.7 | 96.7 | 100 | — |
| | | | Polymers | 2.2 lb | 0 | 6.7 | 6.7 | 6.7 | — |
| | | | Control | — | 0 | 5 | 10 | 10 | — |
| 4 | A.T. | 4th/P | Polymers + Arosurf MSF + B.t.i. (14 days) | 4.4 lb | 83.3 | 96.7 | 96.7 | 100 | — |
| | | | Arosurf MSF + B.t.i. (14 days) | 0.26 gal | 76.7 | 93.3 | 96.7 | 100 | — |
| | | | B.t.i. + water (1 day) | 5.0 gal | 40 | 63.3[6] | — | — | — |
| | | | Arosurf MSF | 0.26 gal | 60 | 86.7 | 96.7 | 100 | — |
| | | | Control | — | 5 | 5 | 15 | 15 | — |
| 5 | A.T. | 4th/P | Polymers + Arosurf MSF + B.t.i. (12 days) | 4.4 lb | 93.3 | 100 | — | — | — |
| | | | Arosurf MSF + B.t.i. (12 days) | 0.26 gal | 76.7 | 93.3 | 100 | — | — |
| | | | B.t.i. + water (1 day) | 5.0 gal | 30 | 43.3 | 53.3[7] | — | — |
| | | | Arosurf MSF + water (1 day) | 5.0 gal | 96.7 | 96.7 | 100 | — | — |
| | | | Polymers | 2.2 lb | 6.7 | 6.7 | 6.7 | — | — |
| | | | Control | — | 10 | 10 | 10 | — | — |
| 6 | C.Q. | 3rd | Polymers + Arosurf MSF + B.t.i. (1 day) | 4.4 lb | 86.7 | 100 | — | — | — |
| | | | B.t.i. + water (1 day) | 5.0 gal | 90 | 100 | — | — | — |
| | | | Arosurf MSF | 0.26 gal | 6.7 | 30 | 33.3 | 36.7 | 43.3 |
| | | | Polymers | 2.2 lb | 0 | 0 | 0 | 0 | 6.7 |
| | | | Control | — | 0 | 0 | 0 | 0 | 3.3 |
| 7 | C.Q. | 4th (late) | Polymers + Arosurf MSF + B.t.i. (1 day) | 4.4 lb | 53.3 | 76.7 | 80 | 100 | — |
| | | | Polymers + Arosurf MSF + B.t.i. (28 days) | 4.4 lb | 63.3 | 90 | 93.3 | 100 | — |
| | | | B.t.i. + water (1 day) | 5.0 gal | 53.3 | 53.3 | 53.3 | 53.3[7] | — |
| | | | Arosurf MSF | 0.26 gal | 13.3 | 20 | 53.3 | 66.7 | — |
| | | | Control | — | 0 | 3.3 | 3.3 | 3.3 | — |
| 8 | C.Q. | 4th/P | Polymers + Arosurf MSF + B.t.i. (40 days) | 4.4 lb | 50 | 100 | — | — | — |
| | | | Polymers + Arosurf MSF + B.t.i. (1 day) | 4.4 lb | 63.3 | 96.7 | 100 | — | — |
| | | | Arosurf MSF + B.t.i. (40 days) | 0.26 gal | 60 | 90 | 100 | — | — |
| | | | Arosurf MSF + B.t.i. (1 day) | 0.26 gal | 63.3 | 100 | — | — | — |
| | | | B.t.i. + water (1 day) | 5.0 gal | 33.3 | 33.3[8] | — | — | — |
| | | | Arosurf MSF | 0.26 gal | 20 | 40 | 76.7 | 100 | — |
| | | | Control | — | 0 | 0 | 3.3 | 6.7 | — |
| 9 | A.A. | 4th (late) | Polymers + Arosurf MSF + B.t.i. (1 day) | 4.4 lb | 93.3 | 100 | — | — | — |
| | | | Polymers + Arosurf MSF + B.t.i. (28 days) | 4.4 lb | 86.7 | 100 | — | — | — |
| | | | B.t.i. + water | 5.0 gal | 73.3 | 73.3[9] | — | — | — |
| | | | Arosurf MSF | 0.26 gal | 0 | 0 | — | — | — |
| | | | Control | — | 0 | 0 | — | — | — |

[1]Starch, acrylonitrile copolymer (Super Sorb) used in all tests. Arosurf MSF lot no. 4158k used in all tests. B.t.i. used in tests nos. 1 and 6 was Teknar HP-D (1200 ITU per milligram) while tests 2, 7, and 8 were conducted with Teknar ® (600 ITU per milligram); Zoecon Corporation, Dallas, Texas 75234. Tests 3, 4, and 5 were conducted with Bactimos ® primary powder (7000 ITU per milligram); Biochem Products, Montchanin, Delaware 19710.
[2]A.T. tests nos. 1 and 2 conducted in 12.5% seawater while A.T. tests nos. 3, 4, and 5 were conducted in 100% seawater. C.Q. tests nos. 6 and 8 conducted in R.O. water and C.Q. no. 7 was conducted in effluent collected from a sewage treatment system. A.A. test no. 9 conducted in R.O. water.
[3]B.t.i. in tests nos. 1, 2, 6, 7, and 8 applied at a rate of 0.5 pt/acre. B.t.i. in tests nos. 3 and 4 applied at a rate of 0.0625 kg/ha while test no. 5 was applied at a rate of 0.03125 kg/ha.
[4]Arosurf MSF in polymer-base and B.t.i. formulations applied at a rate of ca. 0.23 gal/acre.
[5]30% adult escapees.
[6]36.7% adult escapees.
[7]46.7% adult escapees.
[8]66.7% adult escapees.
[9]26.7% adult escapees.
[10]Test terminated at highest mortality shown.

Furthermore, the data indicates that the superabsorbent polymer(s) impregnated with Arosurf® MSF had long term storage stability. Storage stability is also indicated with joint action formulations (Tables IV–VI). In general, mosquito-controlling efficacy of new and old formulations was comparable.

form. The powdered superabsorbent polymers can be formed into a solidified elastic-like matrix without the use of a film-forming, or other insecticidal agent and without the use of conventional agglomeration equipment or techniques. One gram of unimpregnated Water Lock® Superabsorbent Polymer G-100 was spread thinly over the bottom of a

TABLE VII

Effect of storage on efficacy of formulations of superabsorbent polymer-base Arosurf ® MSF against larvae of *Aedes taeniorhynchus*.[1]

| Run no. | Larval instar | Formulation | Formulation age | Application rate per surface acre | Cumulative percentage mortality of larvae, pupae, and/or emerging adults at indicated posttreatment time period (days)[5] 1 | 2 | 3 | 4 | 5 | 6 |
|---|---|---|---|---|---|---|---|---|---|---|
| 1 | 3rd | Polymers + Arosurf MSF | 1 hr | 4.4 lb[2] | 36.7 | 86.7 | 90 | 93.3 | 100 | — |
| | | Polymers + Arosurf MSF | 1 hr | 6.6 lb[3] | 40 | 96.7 | 96.7 | 96.7 | 96.7 | 100 |
| | | Polymers + Arosurf MSF | 7 days | 4.4 lb | 53.3 | 93.3 | 93.3 | 96.7 | 100 | — |
| | | Polymers + Arosurf MSF | 7 days | 6.6 lb | 83.3 | 100 | — | — | — | — |
| | | Control | — | — | 0 | 0 | 3.3 | 3.3 | 3.3 | 3.3 |
| 2 | 2nd | Polymers + Arosurf MSF | 1 hr | 4.4 lb | 6.7 | 53.3 | 80 | 96.7 | 100 | — |
| | | Polymers + Arosurf MSF | 1 hr | 6.6 lb | 13.3 | 86.7 | 96.7 | 100 | — | — |
| | | Polymers + Arosurf MSF | 35 days | 4.4 lb | 16.7 | 80 | 96.7 | 96.7 | 100 | — |
| | | Polymers + Arosurf MSF | 35 days | 6.6 lb | 13.3 | 80 | 93.3 | 96.7 | 100 | — |
| | | Control | — | — | 0 | 0 | 6.7 | 13.3 | 13.3 | — |
| 3 | 3rd | Polymers + Arosurf MSF | 1 hr | 4.4 lb | 66.7 | 100 | — | — | — | — |
| | | Polymers + Arosurf MSF | 1 hr | 6.6 lb | 63.3 | 100 | — | — | — | — |
| | | Polymers + Arosurf MSF | 1 hr | 8.8 lb[4] | 73.3 | 100 | — | — | — | — |
| | | Polymers + Arosurf MSF | 62 days | 4.4 lb | 26.7 | 100 | — | — | — | — |
| | | Polymers + Arosurf MSF | 62 days | 6.6 lb | 63.3 | 100 | — | — | — | — |
| | | Polymers + Arosurf MSF | 62 days | 8.8 lb | 73.3 | 100 | — | — | — | — |
| | | Control | — | — | 3.3 | 3.3 | | | | |
| 4 | 3rd | Polymers + Arosurf MSF | 1 hr | 4.4 lb | 26.7 | 63.3 | 100 | — | — | — |
| | | Polymers + Arosurf MSF | 77 days | 4.4 lb | 23.3 | 53.3 | 100 | — | — | — |
| | | Control | — | — | 3.3 | 3.3 | 3.3 | — | — | — |
| 5 | 4th | Polymers + Arosurf MSF | 1 hr | 6.6 lb | 73.3 | 90 | 93.3 | 96.7 | 100 | — |
| | | Polymers + Arosurf MSF | 110 days | 6.6 lb | 86.7 | 100 | — | — | — | — |
| | | Control | — | — | 0 | 0 | 0 | 0 | 0 | — |
| 6 | 3rd | Polymers + Arosurf MSF | 1 hr | 6.6 lb | 30 | 86.7 | 100 | — | — | — |
| | | Polymers + Arosurf MSF | 124 days | 6.6 lb | 26.7 | 90 | 100 | — | — | — |
| | | Control | — | — | 0 | 3.3 | 3.3 | — | — | — |
| 7 | 3rd | Polymers + Arosurf MSF | 1 hr | 6.6 lb | 0 | 50 | 90 | 96.7 | 100 | — |
| | | Polymers + Arosurf MSF | 130 days | 6.6 lb | 13.3 | 56.7 | 100 | — | — | — |
| | | Control | — | — | 0 | 3.3 | 6.7 | — | — | — |

[1]Starch, acrylonitrile copolymer (Super Sorb) used in all tests. Arosurf MSF lot no. 4158K used in all tests. All bioassys conducted in 12.5% artificial seawater.
[2]1:1 ratio of Polymers to Arosurf MSF with Arosurf MSF application rate of 0.23 gal/acre.
[3]1:1 ratio of Polymers to Arosurf MSF with Arosurf MSF application rate of 0.35 gal/acre.
[4]1:1 ratio of Polymers to Arosurf MSF with Arosurf MSF application rate of 0.46 gal/acre.
[5]Tests terminated at highest mortality shown.

Powdered, encapsulated, pelletized, or briqueted formulations of nonimpregnated superabsorbent polymers can be introduced into the wells of abandoned tires, tree holes, bromeliads, cans, birdbaths, or other small natural or artificial water-holding receptacles against certain Aedes, Culex, and Wyeomyia mosquitoes when they are dry, for pretreatment, or when full of collected rain water, and contain eggs, larvae and pupae. This application will prevent egg hatching and breeding for prolonged periods, or physically kill mosquitoes in their larval or pupal stages simply by gelling the water that is necessary for immature development. Both quick and extended control of immature mosquitoes are expected to result from this physical control technique, and the use of various gel formulations are noted herein. It should also be noted that the superabsorbent polymers used in these applications may also be impregnated with any number of insecticidal agents as described herein.

EXAMPLE VIII

The superabsorbent polymers useful in the practice of this invention are generally in powdered, flaked or extruded standard weighing boat and was allowed to be exposed to the air in an air conditioned room (70°–75° F.) for 24 hours. Observation showed that the powdered superabsorbent polymer had bonded into a unified elastic-like matrix that could be molded into a variety of shapes. The material was hand agglomerated into a ball and added to 250 ml of water. This material was observed to swell and gel the water in a manner similar to the un-unified powdered superabsorbent polymer; however, at a slower rate. Variation in this technique could effect slow or controlled water gelling and/or release of impregnated active ingredients, and thereby control the action of the superabsorbent polymer in controlling a population of aquatic environment insects. The release rate may be further modified by compaction variations in the types of superabsorbent polymers mixed, etc.

EXAMPLE IX

Pre-gelled formulations of superabsorbent polymer and film-forming or other insecticidal agents can be produced in the manner described above, with the addition of various concentrations of water. By varying the relative amounts of powdered superabsorbent polymers and water added thereto, various matrix (gel) consistencies were achieved. Initial tests indicate that different rates of release of Arosurf® MSF could be achieved in this manner. In addition, other insecticidal ingredients can also be incorporated into the gel. These compositions may additionally be compacted, etc. to further modify the release rate.

EXAMPLE X

Additional tests indicate that powdered superabsorbent polymers or powdered superabsorbent polymers impregnated with film-forming/surface active agents and/or other conventional pesticides, ovicides, larvicides, pupicides, biological control agents, microbial control agents, pathogens, parasites, insect growth regulators and/or other insecticidal agents can be packaged or encapsulated within nontoxic and biodegradable 1.5 to 3 mil polyvinyl alcohol-base, or polyethylene oxide-base, or hydroxypropyl methyl cellulose-base, water soluble pouches for direct introduction into aquatic habitats for the control of a population of immature aquatic insects. Tests with 2×2 inch and 3×4 inch pouches of polyvinyl alcohol filled with 1:1, 1:2, and 1:3 Super Sorb and Arosurf ® MSF mixtures showed that the bags would float and differentially solubilize when thrown into water, thereby releasing the superabsorbent polymer and various concentrations of mosquitocidal film-forming agent at different rates. The mil thickness of the pouches was observed to affect the rate of water solubility and the storage stability of the pouches. Surprisingly, tests further indicated that polyvinyl alcohol bags filled with the 1:1 mixture dissolved at a slower rate than polyvinyl alcohol bags without the presence of these materials. Certain film-forming/surface active agents, when in contact with the pouch, may retard the rate of solubilization of the pouch when placed in water. Therefore, variations of the pouch thickness, rate of solubilization, and hence release of the superabsorbent polymer with or without insecticidal agent, can be achieved. The insecticidal delivery compound may additionally be compacted, etc. to further modify the release rate.

EXAMPLE XI

Powdered or flaked superabsorbent polymers and formulations which include insecticidal agents can be formed into a variety of shapes and sizes by standard agglomeration techniques.

Agglomeration is a term used to describe a process whereby minute particles composed of dust, powders, mineral or chemical fines, etc. are increased in size by combining them. This process, the conversion of solid fines to larger, more manageable shapes, is called agglomeration. Other similar particulate matter may require size enlargement to make it more saleable or to improve its physical properties and performance. The same processes are employed, and this, too, is agglomeration. The three general categories of agglomeration include agitation or pelletizing (balling devices, disc pelletizers, drums and cones and some types of mixers), compaction or compression (briquetting, compacting, tableting and extrusion), and heat treatment (sintering, as with powdered metals), nodulizing and the production of granules from molten material. A brochure, FT306 11/84-827084-2M© FT 1984, from Ferro-Tech Systems, "The Solution For Material Processing Problems and Pest Control", describes the aforementioned, for instance a turbulator (a type of blending or mixing apparatus) mixture of powdered Super Sorb and Arosurf® MSF (800 g:1000 g) was formulated into 1/16 inch granules on a disc pelletizer. These granules were shown to exhibit the ability to control populations of immature mosquitoes with efficacy comparable to non-agglomerated formulations (Table III); however, at a lower total bulk application rate. 1/8 inch granules (pellets) were also produced in the same manner. The addition of a binder such as water, clay, cetyl or stearyl alcohols, etc. may be used in the formulation to make harder granules and/or to enhance their ability to float or sink. These granules may additionally be compacted into a variety of shapes, etc. with a resulting change in the rate of insecticidal agent delivery.

EXAMPLE XII

Nonconventional agglomeration techniques can be used to produce solid unified matrices from powdered superabsorbent polymers and superabsorbent polymers/insecticidal agent formulations. A 1:1 mixture of Super Sorb or Water Lock® G-100 and Arosurf® MSF or sorbitan monooleate were hand compacted into standard rectangular plastic tissue embedding molds. The mixtures were allowed to sit for 24–48 hours under fluctuating air temperatures and humidity conditions (ca. 70°–83° F.; ca. 50–80%RH). Results showed that the temperature/humidity fluctuations produced hard briquet-like matrices in the shape of the molds. This technique was also used to produce a briquet from mixtures of Water Lock® G-100 or Super Sorb and Arosurf® MSF and Bactimos® Primary Powder (*Bacillus thuringiensis* var. *israelensis*).

EXAMPLE XIII

In one test, 2.0 g Water Lock® G-100 superabsorbent polymer, 0.1 g Morwet® EFW surfactant powder, and 0.5 g B.t.i. (Bactimos® Primary Powder) were mixed together in a 50 ml beaker and allowed to stand exposed to 80° F./80% RH (Ambient) for about 24 hours. These environmental conditions caused the three ingredients (total 2.6 g) to bind together (cross-link) into a single elastic-like matrix.

This cookie-like material was introduced into an 8.5×11 inch pan containing water and several hundred 2nd-4th instar larvae of *Cx. quinquefasciatus*. The surface of the water was lightly dusted with talc to observe the spreading potential of the powdered surfactant.

The matrix was observed to float on introduction to the water and push and compact the talc to the opposite end of the pan, and then begin to typically swell and release the B.t.i. and surfactant as it slowly absorbed water. One hundred percent of the larvae were killed in 5 hours post-treatment indicating the use of powdered surfactants in the formulation of superabsorbent polymers and B.t.i., or B. sphaericus, etc. for self-spreading, quick and/or slow release mosquito control applications.

EXAMPLE XIV

Powdered Super Sorb superabsorbent polymer impregnated with Arosurf ® MSF was tightly compacted into a plastic test tube which was open at one end. The tube containing the insecticidal delivery agent was observed to float on the water and slowly release the active film-forming/polymer materials for a period of approximately 10 days. The equivalent amount of loosely packed material released the entire contents of the tube within 24 hours. The presence or persistence of Arosurf® MSF or the surface of the water was monitored with Adol® indicator oil. Thus, release rates can be varied by modifying the degree of compaction and/or the size of the release orifice. Standard compaction techniques may be used (possibly with addition of a binding agent) to produce self-contained briquettes or pellets that have significant slow or controlled release abilities.

EXAMPLE XV

As noted earlier, powdered superabsorbent polymers have the ability to reform or contract and then re-gel. In one test, one gram of powdered Super Sorb or Water Lock® G-100 that had absorbed (gelled) 250 ml of water in a beaker, was allowed to stand at room temperature (70°–75° F.), in a room for several days until the absorbed water had evaporated. The powdered matrix returned to a semi-original congealed form. 250 ml of water was then re-administered to the beaker. The polymer was observed to gel in a manner similar to the original absorption. This process was repeated five additional times with similar results. A comparable test was conducted on a 1:1 mixture of Super Sorb and Arosurf® MSF with similar results.

EXAMPLE XVI

The water-superabsorbent characteristics of superabsorbent polymers are useful to effect a physical (non-toxic) method for controlling certain populations of nuisance and/ or disease carrying mosquitoes (e.g. *Aedes aegypti* and *Ae. albopictus*) that mainly breed in small rainwater collecting receptacles (e.g. abandoned tires, planters, tree holes, etc.). Water Lock® G-100 (non-impregnated) was placed in a 400 ml glass beaker containing 100–200 eggs of *Aedes aegypti* (3 replications/polymer type). Controls containing no superabsorbent polymer were used to monitor the validity of the example. 250 ml of water was then added to the beakers to induce eclosion.

Results showed that water introduced into the beakers containing Water Lock® G-100 would instantly gel, thereby producing a non-aquatic environment that was unsuitable for egg hatching and larval development. Eggs in beakers containing no superabsorbent polymer produced normal larvae. Similar results were obtained using Super Sorb.

EXAMPLE XVII

One gram of powdered Super Sorb or Water Lock® G-100 superabsorbent polymer (non-impregnated) was added to beakers containing 250 ml of water and ten 2nd instar larvae of *Aedes aegypti*. The larvae were instantly gelled within the formed matrix and subsequently died. This example was repeated using 2nd to 4th instar larvae and pupae of *Culex quinquefasciatus* with similar results.

The principles, preferred embodiments and modes of operation of the present invention have been described in the foregoing specification. The invention which is intended to be protected herein, however, is not to be construed as limited to the particular forms disclosed, since these are to be regarded as illustrative rather than restrictive. Variations and changes may be made by those skilled in the art without departing from the spirit of the invention.

What I claim is:

1. A controlled release insecticidal delivery composition for controlling a population of aquatic environment insects in preflood or flood conditions comprising (1) at least one superabsorbent organic polymer, wherein said superabsorbent polymer is selected from at least one of the group consisting of: hydrolyzed starch-polyacrylonitrile and metal salts thereof; 2-propenenitrile, homopolymer, hydrolyzed, sodium salt; starch-g-poly(acrylonitrile) and metal salts thereof; starch-g-poly(acrylamide-co-sodium acrylate); poly (2-propenamide-co-2-propenoic acid, sodium salt); starch-g-poly(2-propenamide-co-2-propenoic acid, potassium salt); starch-g-poly(2-propenamide-co-2-propenoic acid); starch-g-poly(2-propenamide-co-2-propenoic acid, sodium salt); poly-2-propenoic acid, sodium salt; starch grafted sodium polyacrylates and metal salts thereof; crosslinked polyacrylamide and metal salts thereof; and copolymer acrylamide acrylate and metal salts thereof; which polymer will, when in contact with water, absorb over 100 times its weight in water, (2) at least one insecticidal agent, said polymer and insecticidal agent being present in a total amount effective to control the population of aquatic environment insects; and (3) inert diluent ingredients, wherein the weight ratio of superabsorbent polymer to insecticidal agent and inert diluent ingredients is from about 0.1:100 to about 100:0.001, and wherein said composition is an admixture formed by mixing the superabsorbent polymer, the insecticidal agent, and the inert diluent ingredients such that the superabsorbent polymer is impregnated with the insecticidal agent and with the inert diluent ingredients to control the release rate in the aquatic environment, and wherein said composition will, when in contact with water in the aquatic environment, after being applied by delivering said composition to a target habitat of an aquatic environment insect, be effective in the environment to control the population of insects in that said composition will absorb water and provide variable time release of the insecticidal agent, thereby allowing for controlled release of the insecticidal agent into the aquatic environment to kill insects in various stages selected from the group consisting of eggs, larvae, pupae, nymphs, emerging adults, adults, and combinations thereof.

2. The controlled release insecticidal delivery composition of claim 1, wherein the copolymer acrylamide acrylate and metal salts thereof is an acrylamide sodium acrylate copolymer.

3. The controlled release insecticidal delivery composition of claim 1, wherein said polymer will, when in contact with water, absorb over 500 times its weight in water.

4. The controlled release insecticidal delivery composition of claim 1, wherein said composition is anionic, cationic or nonionic.

5. The composition of claim 1, which contains a surface active agent.

6. The controlled release insecticidal delivery composition of claim 1, wherein the composition is placed within a container having walls made of at least one water-soluble material.

7. The controlled release insecticidal delivery composition of claim 6, wherein said walls of said container consist of at least one water-soluble material selected from the group consisting of polyvinyl alcohol, polyethylene oxide and hydroxypropyl methyl cellulose.

8. A controlled release insecticidal delivery composition for controlling a population of aquatic environment insects in preflood or flood conditions comprising (1) at least one superabsorbent organic polymer, wherein said superabsorbent polymer is selected from at least one of the group consisting of: hydrolyzed starch-polyacrylonitrile and metal salts thereof; 2-propenenitrile, homopolymer, hydrolyzed, sodium salt; starch-g-poly(acrylonitrile) and metal salts thereof; starch-g-poly(acrylamide-co-sodium acrylate); poly (2-propenamide-co-2-propenoic acid, sodium salt); starch-g-poly(2-propenamide-co-2-propenoic acid, potassium salt); starch-g-poly(2-propenamide-co-2-propenoic acid); starch-g-poly(2-propenamide-co-2-propenoic acid, sodium salt); poly-2-propenoic acid, sodium salt; starch grafted sodium polyacrylates and metal salts thereof; crosslinked polyacrylamide and metal salts thereof; and copolymer acrylamide acrylate and metal salts thereof; which polymer will, when in contact with water, absorb over 100 times its weight in water, (2) at least one insecticidal agent comprising a film-forming agent, said polymer and insecticidal agent being present in a total amount effective to control the population of aquatic environment insects; and (3) inert diluent ingredients, wherein the weight ratio of superabsorbent polymer to insecticidal agent and inert diluent ingredients is from about 0.1:100 to about 100:0.001, and wherein said composition is an admixture formed by mixing the superabsorbent polymer, the insecticidal agent, and the inert diluent ingredients such that the superabsorbent polymer is impregnated with the insecticidal agent and with the inert diluent ingredients to control the release rate in the aquatic environment, and wherein said composition will, when in contact with water in the aquatic environment, after being applied by delivering said composition to a target habitat of an aquatic environment insect, be effective in the environment to control the population of insects in that said composition will absorb water and provide variable time release of the insecticidal agent, thereby allowing for controlled release of the insecticidal agent into the aquatic environment to kill insects in various stages selected from the group consisting of eggs, larvae, pupae, nymphs, emerging adults, adults, and combinations thereof.

9. The controlled release insecticidal delivery composition of claim 8, wherein the copolymer acrylamide acrylate and metal salts thereof is an acrylamide sodium acrylate copolymer.

10. A controlled release mosquitocidal delivery composition for controlling a population of aquatic environment mosquitoes comprising (1) at least one superabsorbent organic polymer, wherein said superabsorbent polymer is selected from at least one of the group consisting of: hydrolyzed starch-polyacrylonitrile and metal salts thereof; 2-propenenitrile, homopolymer, hydrolyzed, sodium salt; starch-g-poly(acrylonitrile) and metal salts thereof; starch-g-poly(acrylamide-co-sodium acrylate); starch-g-poly(2-propenamide -co-2-propenoic acid, potassium salt); starch-g-poly(2-propenamide-co-2-propenoic acid); starch-g-poly (2-propenamide -co-2-propenoic acid, sodium salt); poly-2-propenoic acid, sodium salt; starch grafted sodium polyacrylates and metal salts thereof; crosslinked polyacrylamide and metal salts thereof; and copolymer acrylamide acrylate and metal salts thereof; which polymer will, when in contact with water, absorb over 100 times its weight in water, (2) at least one insecticidal agent comprising a film-forming agent, and (3) at least one additional compound selected from the group consisting of toxicants and biological control agents, said polymer, insecticidal agent and additional compound being present in a total amount effective to control the population of aquatic environment mosquitoes, and wherein the ratio of superabsorbent polymer to insecticidal agent is from about 0.1:1 to 100:1, which composition is an admixture formed by mixing the superabsorbent polymer, the insecticidal agent, and the additional compound such that the superabsorbent polymer is impregnated with the insecticidal agent and with the additional compound, and which composition will, when in contact with water in the aquatic environment, absorb water and provide variable time release of the insecticidal agent, thereby allowing for controlled release of the insecticidal agent into the aquatic environment to kill insects in various stages selected from the group consisting of eggs, larvae, pupae, nymphs, emerging adults, adults, and combinations thereof.

11. The controlled release mosquitocidal delivery composition of claim 10, wherein the copolymer acrylamide acrylate and metal salts thereof is an acrylamide sodium acrylate copolymer.

12. The controlled release mosquitocidal delivery composition of claim 10, wherein the toxicants are pesticides.

13. The controlled release mosquitocidal delivery composition of claim 12, wherein the pesticides are selected from the group consisting of ovicides; larvicides; pupicides; and insecticides.

14. The controlled release mosquitocidal delivery composition of claim 11, wherein the biological control agents are selected from the group consisting of microbial control agents; pathogens; parasites; and insect growth regulators.

* * * * *